(12) United States Patent
Lallemand et al.

(10) Patent No.: US 12,006,529 B2
(45) Date of Patent: Jun. 11, 2024

(54) METHOD AND SYSTEM FOR IDENTIFYING THE GRAM TYPE OF A BACTERIUM

(71) Applicant: BIOMERIEUX, Marcy l'Etoile (FR)

(72) Inventors: Jordane Lallemand, Villeneuve les Maguelone (FR); Denis Leroux, Trevoux (FR); Manuel Petit, Grenoble (FR)

(73) Assignee: BIOMERIEUX, Marcy l'Etoile (FR)

( * ) Notice: Subject to any disclaimer, the term of this patent is extended or adjusted under 35 U.S.C. 154(b) by 0 days.

(21) Appl. No.: 16/772,402

(22) PCT Filed: Dec. 20, 2018

(86) PCT No.: PCT/FR2018/053434
§ 371 (c)(1),
(2) Date: Jun. 12, 2020

(87) PCT Pub. No.: WO2019/122732
PCT Pub. Date: Jun. 27, 2019

(65) Prior Publication Data
US 2021/0079441 A1 Mar. 18, 2021

(30) Foreign Application Priority Data
Dec. 21, 2017 (FR) ...................................... 1762814

(51) Int. Cl.
*G01N 21/31* (2006.01)
*C12Q 1/04* (2006.01)
*G01J 3/28* (2006.01)

(52) U.S. Cl.
CPC .............. *C12Q 1/04* (2013.01); *G01J 3/2803* (2013.01); *G01J 3/2823* (2013.01); *G01N 21/31* (2013.01); *G01N 2201/129* (2013.01)

(58) Field of Classification Search
CPC ........ G01N 2201/129; G01J 3/28; C12Q 1/04
See application file for complete search history.

(56) References Cited

U.S. PATENT DOCUMENTS

| 4,512,660 A | 4/1985 | Goldberg |
| 5,510,246 A | 4/1996 | Morgan |

(Continued)

FOREIGN PATENT DOCUMENTS

| CN | 104136908 A | 11/2014 |
| CN | 105651679 A | 6/2016 |

(Continued)

OTHER PUBLICATIONS

Phumudzo Tshikhudo,"Bacterial species identification getting easier", 2013 (Year: 2013).*

(Continued)

*Primary Examiner* — Maurice C Smith
(74) *Attorney, Agent, or Firm* — Seckel IP, PLLC

(57) ABSTRACT

The invention relates to a method for detecting the Gram type and the fermenting character of a bacterial strain, said method comprising: illuminating, in the wavelength range of 390 nm to 900 nm, at least one bacterium from said strain which has a natural electromagnetic response within said range; acquiring, within said range, a light intensity reflected by, or transmitted through, said illuminated bacterium; and determining the Gram type and the fermenting character of the bacterial strain according to the light intensity acquired within said range.

27 Claims, 19 Drawing Sheets

(56) References Cited

U.S. PATENT DOCUMENTS

| | | |
|---|---|---|
| 8,652,800 B2 | 2/2014 | Walsh et al. |
| 8,748,122 B2 | 6/2014 | Hyman et al. |
| 8,795,983 B2 | 8/2014 | Hyman et al. |
| 9,822,389 B2 | 11/2017 | Hyman et al. |
| 2003/0082516 A1 | 5/2003 | Straus |
| 2007/0279629 A1 | 12/2007 | Grun et al. |
| 2009/0303472 A1 | 12/2009 | Zhao et al. |
| 2010/0014078 A1 | 1/2010 | Dholakia et al. |
| 2010/0068755 A1 | 3/2010 | Walsh et al. |
| 2010/0129858 A1 | 5/2010 | Walsh et al. |
| 2010/0136609 A1 | 6/2010 | Clay et al. |
| 2011/0033847 A1 | 2/2011 | Hyman et al. |
| 2011/0281291 A1 | 11/2011 | Ullery et al. |
| 2012/0135454 A1 | 5/2012 | Walsh et al. |
| 2013/0323718 A1 | 12/2013 | Hyman et al. |
| 2014/0335558 A1 | 11/2014 | Hyman et al. |
| 2014/0377795 A1 | 12/2014 | Gannot et al. |
| 2017/0073725 A1 | 3/2017 | Upton et al. |
| 2017/0236281 A1 | 8/2017 | Dacosta |
| 2018/0128747 A1 | 5/2018 | Zhao et al. |
| 2018/0245124 A1 | 8/2018 | Bork |
| 2019/0195802 A1 | 6/2019 | Attar et al. |
| 2019/0293620 A1 | 9/2019 | Farkas et al. |
| 2019/0323948 A1 | 10/2019 | Leroux et al. |
| 2021/0079442 A1 | 3/2021 | Lallemand et al. |

FOREIGN PATENT DOCUMENTS

| | | | |
|---|---|---|---|
| EP | 3257947 A1 | 12/2017 | |
| JP | 2001-272399 A | 10/2001 | |
| JP | 2011-529187 A | 12/2011 | |
| JP | 2015-507182 A | 3/2015 | |
| KR | 20110091717 A | 8/2011 | |
| WO | 2010011798 A1 | 1/2010 | |
| WO | 2010077304 A2 | 7/2010 | |
| WO | WO-2010132823 A2 * | 11/2010 | ............... C12Q 1/24 |
| WO | 2016137341 A1 | 9/2016 | |

OTHER PUBLICATIONS

International Search Report and Written Opinion dated Apr. 26, 2019 in counterpart application No. PCT/FR2018/053434 (with English partial translation and partial machine translation; total 22 pages).

H.S. Kim et al., "Development of a multispectral light-scatter sensor for bacterial colonies", Journal of Biophotonics, vol. 10, No. 5, Jul. 14, 2016, pp. 634-644 (in English; D2 cited in the ISR).

M. Guillemot et al., "Hyperspectral imaging for presumptive identification of bacterial colonies on solid chromogenic culture media", Proceedings of SPIE, SPIE, Bellingham, WA, vol. 9887, Apr. 27 206, pp. 98873L-1 to 98873L-12 (total 12 pages) (in English; D3 cited in the ISR).

S. Arrigoni et al., "Hyperspectral image analysis for rapid and accurate discrimination of bacterial infections: A benchmark study", Computers in Biology and Medicine, vol. 88, Jun. 21, 2017, pp. 60-71 (in English; D4 cited in the ISR).

M. Graus et al., "Hyperspectral fluorescence microscopy detects autofluorescent factors that can be exploited as a diagnostic method for species differentiation", Journal of Biomedical Optics, vol. 22, No. 1, Jan. 2017, cover page and pp. 016002-1 to 016002-6 (total 7 pages) (in English; D5 cited in the ISR).

B. Park et al., "Hyperspectral microscope imaging methods to classify grampositive and gram-negative foodborne pathogenic bacteria", Transactions of the ASABE, American Society of Agricultural and Biological Engineers, St. Joseph, MI, vol. 58, No. 1, Jan. 1, 2015, pp. 5-16 (in English; D6 cited in the ISR).

International Search Report and Written Opinion dated Mar. 21, 2019 in application No. PCT/FR2018/053436 corresponding to co-pending U.S. Appl. No. 16/772,410 (with English partial translation and partial machine translation; total 28 pages).

J.D. Walsh et al., "Rapid Intrinsic Fluorescence Method for Direct Identification of Pathogens in Blood Cultures", mBio, vol. 4, No. 6, Nov. 19, 2013, e00865-13, pp. 1-9 (Note: in English; D1 cited in the ISR of co-pending U.S. Appl. No. 16/772,410).

Office Action dated Aug. 15, 2022 in co-pending U.S. Appl. No. 16/772,410 (witn PTO892, without returned SB08; total 11 pages) (Note: US20170236281, ref.B cited in the Office Action is not listed in this IDS since it was already listed in the IDS filed Aug. 10, 2020 in this application).

Japanese Office Action dated Oct. 4, 2022 in counterpart application JP 2020-533214 (with English translation; total 8 pages) (Note: Arrigoni et al 2017, D1; Walsh et al. 2013, D3, and Guillemot 2016, D7 cited in this JP Office Action are not listed in this IDS form since they are already of record).

Turra et al., "Hyperspectral image acquisition and analysis of cultured bacteria for the discrimination of urinary tract infections", 2015 37th Annual International Conference of the IEEE Engineering in Medicine and Biology Society (EMBC), 2015, pp. 759-762 (Note: in English; D6 cited in the JP Office Action dated Oct. 4, 2022).

Japanese Office Action dated Oct. 4, 2022 in application JP 2020-533199, counterpart of co-pending U.S. Appl. No. 16/772,410 (with English translation; total 10 pages) (Note: D1-D7 cited in this JP Office Action are D6, D2-D5, D1, and D7 cited in the JP Office Action dated Oct. 4, 2022 in counterpart application JP 2020-533214).

Office Action dated Mar. 15, 2023 in co-pending U.S. Appl. No. 16/772,410 (with PTO892, without returned SB08; total 20 pages).

CN Office Action dated Nov. 11, 2023 in application No. CN 201880082224.8, counterpart of co-pending U.S. Appl. No. 16/772,410 (with English translation; total 17 pages).

Notice of Allowance dated Sep. 26, 2023 in co-pending U.S. Appl. No. 16/772,410 (with PTO892, without returned SB08; total 11 pages).

CN Office Action dated Sep. 26, 2023 in counterpart application No. CN 201880082258.7 (with English machine translation; total 16 pages).

Korean Office Action dated Jun. 21, 2023 in counterpart application KR 10-2020-7021133 (with English translation; total 17 pages).

Korean Office Action dated Jun. 21, 2023 in application KR 10-2020-7021137, counterpart of U.S. Appl. No. 16/772,410 (with English translation; total 15 pages).

* cited by examiner

| Species | Vitek code | Class |
|---|---|---|
| *Citrobacter koseri* | CIT-KOS | GNF |
| *Enterobacter cloacae* | ENT-CLC | GNF |
| *Escherichia coli* | ESH-COL | GNF |
| *Klebsiella pneumoniae* | KLB-PEU | GNF |
| *Morganella morganii* | MOR-MOR | GNF |
| *Enterococcus faecalis* | ENC-FAE | GP |
| *Staphylococcus aureus* | STA-AUR | GP |
| *Staphylococcus epidermidis* | STA-EPI | GP |
| *Streptococcus agalactiae* | STR-AGA | GP |
| *Streptococcus pyogenes* | STR-PYO | GP |
| *Streptococcus viridans (mitis)* | STR-MIT | GP |
| *Candida albicans* | CAN-ALB | Y |
| *Candida guilliermondii* | CAN-GUI | Y |
| *Candida lusitaniae* | CAN-LUS | Y |
| *Candida tropicalis* | CAN-TRO | Y |
| *Candida parapsilosis* | CAN-PRP | Y |
| *Candida dubliniensis* | CAN-DBL | Y |
| *Candida lusitaniae* | CAN-LUS | Y |
| *Burkholderia cepacia* | BUR-CEP | GNNF |
| *Pseudomonas aeruginosa* | PSD-AEU | GNNF |
| *Stenotrophomonas maltophilia* | STE-MLT | GNNF |

Figure 8

|  | COS medium | | | |
| --- | --- | --- | --- | --- |
|  | Block 1 | | Block 2 | |
| Species | Number of colonies | Number of pixels | Number of colonies | Number of pixels |
| ACN-BAU | 20 | 1777 | 19 | 1892 |
| ALC-FAE | 2 | 106 | 2 | 92 |
| BUR-CEP | 27 | 810 | 26 | 630 |
| CAN-ALB | 30 | 1525 | 29 | 1255 |
| CAN-DBL | 28 | 1423 | 27 | 1550 |
| CAN-GUI | 51 | 2832 | 51 | 2887 |
| CAN-KEF | 26 | 3434 | 26 | 3830 |
| CAN-KRU | 11 | 855 | 11 | 806 |
| CAN-LUS | 25 | 1556 | 25 | 1581 |
| CAN-PRP | 29 | 1936 | 28 | 2184 |
| CAN-TRO | 21 | 2379 | 21 | 2358 |
| CIT-KOS | 19 | 3135 | 19 | 3316 |
| ENC-FAE | 59 | 4467 | 59 | 4527 |
| ENT-CLC | 9 | 1635 | 9 | 1696 |
| ESH-COL | 10 | 1424 | 10 | 1936 |
| KLB-PEU | 6 | 3238 | 5 | 3143 |
| MOR-MOR | 5 | 4549 | 5 | 2360 |
| PSD-AEU | 11 | 2035 | 10 | 2284 |
| STA-AUR | 15 | 1458 | 14 | 1402 |
| STA-EPI | 17 | 964 | 16 | 730 |
| STE-MLT | 21 | 1686 | 20 | 1684 |
| STR-AGA | 54 | 2264 | 53 | 1758 |
| STR-MIT | 49 | 1531 | 49 | 1616 |
| STR-PYO | 77 | 1548 | 76 | 1654 |
| TOTAL | 622 | 48567 | 610 | 47171 |

Figure 9

|  | TSA medium | | | |
|---|---|---|---|---|
|  | Block 1 | | Block 2 | |
| Species | Number of colonies | Number of pixels | Number of colonies | Number of pixels |
| ACN-BAU | 8 | 542 | 7 | 476 |
| ALC-FAE | 2 | 73 | 2 | 76 |
| BUR-CEP | 14 | 418 | 13 | 373 |
| CAN-ALB | 6 | 623 | 5 | 529 |
| CAN-DBL | 6 | 390 | 5 | 372 |
| CAN-GUI | 23 | 2102 | 22 | 2191 |
| CAN-KEF | 14 | 2382 | 14 | 1676 |
| CAN-KRU | 33 | 807 | 32 | 775 |
| CAN-LUS | 24 | 2140 | 24 | 2074 |
| CAN-PRP | 21 | 1454 | 20 | 1083 |
| CAN-TRO | 6 | 1457 | 5 | 1378 |
| CIT-KOS | 8 | 1816 | 8 | 1976 |
| ENC-FAE | 36 | 1297 | 35 | 1448 |
| ENT-CLC | 24 | 3129 | 24 | 2455 |
| ESH-COL | 2 | 251 | 2 | 390 |
| KLB-PEU | 2 | 2144 | 1 | 1220 |
| MOR-MOR | 7 | 1151 | 7 | 1359 |
| PSD-AEU | 3 | 355 | 3 | 414 |
| STA-AUR | 23 | 1619 | 22 | 1298 |
| STA-EPI | - | - | - | - |
| STE-MLT | 22 | 894 | 21 | 1078 |
| STR-AGA | 12 | 831 | 12 | 702 |
| STR-MIT | 8 | 140 | 7 | 125 |
| STR-PYO | 24 | 1121 | 23 | 950 |
| TOTAL | 328 | 27136 | 314 | 24418 |

Figure 10

|  |  | Predicted class | | | | TOTAL | Sensitivity |
|---|---|---|---|---|---|---|---|
|  |  | A | B | C | D |  |  |
| Real Class | A | $n_{AA}$ | $n_{AB}$ | $n_{AC}$ | $n_{AD}$ | $n_{A*}$ | $n_{AA} / n_{A*}$ |
|  | B | $n_{BA}$ | $n_{BB}$ | $n_{BC}$ | $n_{BD}$ | $n_{B*}$ | $n_{BB} / n_{B*}$ |
|  | C | $n_{CA}$ | $n_{CB}$ | $n_{CC}$ | $n_{CD}$ | $n_{C*}$ | $n_{CC} / n_{C*}$ |
|  | D | $n_{DA}$ | $n_{DB}$ | $n_{DC}$ | $n_{DD}$ | $n_{D*}$ | $n_{DD} / n_{D*}$ |
|  | TOTAL | $n_{*A}$ | $n_{*B}$ | $n_{*C}$ | $n_{*D}$ | $n_{**}$ |  |
|  | Specificity | $n_{AA}/n_{*A}$ | $n_{BB}/n_{*B}$ | $n_{CC}/n_{*C}$ | $n_{DD}/n_{*D}$ |  |  |

$n_{AA}$ : Number of class A samples properly classified as A by the model (TP)
$n_{AB}$ : Number of class A samples misclassified as B by the model (FN)
$n_{BA}$ : Number of class B samples misclassified as A by the model (FP)
$n_{*A}$ : Number of class A samples
$n_{A*}$ : Number of samples classified as A by the model
$n_{}$ : Total number $$CR = \frac{n_{AA}+n_{BB}+n_{CC}+n_{ADD}}{n_{}} \quad BCR = \frac{(n_{AA}/n_{A*})+(n_{BB}/n_{B*})+(n_{CC}/n_{C*})+(n_{DD}/n_{D*})}{4} = \frac{\Sigma(n_{ii}/n_{i*})}{4}$$

Figure 11

| Branch 1: "GNF" versus "GP+GNN+Y" | | | | Branch 2: "GP" versus "GNN+Y" | | | | Branch 3: "GNN" versus "Y" | | | |
|---|---|---|---|---|---|---|---|---|---|---|---|
| Selection order | Wavelength | BCR (in %) | | Selection order | Wavelength | BCR (in %) | | Selection order | Wavelength | BCR (in %) | |
| | | Calibration | Cross-validation | | | Calibration | Cross-validation | | | Calibration | Cross-validation |
| 1 | 613.58 | 80.5% | 80.4% | 1 | 634.45 | 78.3% | 78.3% | 1 | 613.58 | 95.1% | 95.1% |
| 2 | 484.16 | 89.0% | 89.0% | 2 | 598.97 | 85.7% | 85.6% | 2 | 651.15 | 95.5% | 95.5% |
| 3 | 634.45 | 93.6% | 93.6% | 3 | 665.76 | 87.9% | 87.7% | 3 | 425.71 | 95.8% | 95.7% |
| 4 | 605.23 | 95.1% | 95.1% | 4 | 630.28 | 89.0% | 88.9% | 4 | 617.75 | 95.9% | 95.9% |
| 5 | 588.53 | 95.9% | 95.8% | 5 | 864.07 | 89.8% | 89.7% | 5 | 394.40 | 96.0% | 95.9% |
| 6 | 640.71 | 96.4% | 96.3% | 6 | 548.87 | 90.3% | 90.1% | 6 | 653.24 | 96.0% | 96.0% |
| 7 | 607.31 | 96.8% | 96.7% | 7 | 488.33 | 91.4% | 91.2% | 7 | 659.50 | 96.1% | 96.0% |
| 8 | 434.06 | 97.1% | 97.1% | 8 | 628.19 | 91.7% | 91.6% | 8 | 411.10 | 96.1% | 96.1% |
| 9 | 603.14 | 97.3% | 97.2% | 9 | 661.59 | 92.1% | 92.0% | 9 | 649.06 | 96.2% | 96.2% |
| 10 | 615.66 | 97.4% | 97.4% | 10 | 584.35 | 92.4% | 92.3% | 10 | 404.84 | 96.3% | 96.2% |
| 11 | 630.28 | 97.7% | 97.7% | 11 | 530.08 | 92.7% | 92.6% | 11 | 655.33 | 96.2% | 96.2% |
| 12 | 657.41 | 97.8% | 97.7% | 12 | 636.54 | 92.9% | 92.8% | 12 | 609.40 | 96.3% | 96.2% |
| 13 | 651.15 | 98.0% | 98.0% | 13 | 603.14 | 93.2% | 93.0% | 13 | 586.44 | 96.3% | 96.3% |
| 14 | 601.05 | 98.1% | 98.1% | 14 | 486.25 | 93.4% | 93.3% | 14 | 594.79 | 96.3% | 96.3% |
| 15 | 642.80 | 98.2% | 98.2% | 15 | 546.78 | 93.6% | 93.5% | 15 | 684.55 | 96.4% | 96.3% |
| 16 | 431.97 | 98.3% | 98.3% | 16 | 861.98 | 93.9% | 93.7% | 16 | 553.04 | 96.4% | 96.3% |
| 17 | 488.33 | 98.3% | 98.3% | 17 | 694.99 | 94.0% | 93.8% | 17 | 578.09 | 96.5% | 96.5% |
| 18 | 638.63 | 98.4% | 98.4% | 18 | 429.89 | 94.1% | 94.0% | 18 | 657.41 | 96.6% | 96.5% |
| 19 | 649.06 | 98.4% | 98.4% | 19 | 632.36 | 94.3% | 94.1% | 19 | 636.54 | 96.6% | 96.6% |
| 20 | 598.97 | 98.5% | 98.5% | 20 | 891.20 | 94.4% | 94.3% | 20 | 550.96 | 96.6% | 96.6% |
| 21 | 866.15 | 98.6% | 98.5% | 21 | 582.27 | 94.5% | 94.4% | 21 | 841.10 | 96.7% | 96.6% |
| 22 | 632.36 | 98.6% | 98.6% | 22 | 596.88 | 94.7% | 94.6% | 22 | 615.66 | 96.7% | 96.6% |
| 23 | 592.70 | 98.7% | 98.7% | 23 | 494.60 | 94.8% | 94.7% | 23 | 576.00 | 96.7% | 96.6% |
| 24 | 429.89 | 98.7% | 98.7% | 24 | 532.17 | 94.8% | 94.7% | 24 | 584.35 | 96.8% | 96.7% |

Table 3

Figure 21

Branch 1: "GP" versus "GNF+GNN+Y"

| Selection order | Wavelength | Calibration | Cross-validation |
|---|---|---|---|
| 1 | 482.07 | 65.8% | 65.5% |
| 2 | 429.89 | 72.1% | 71.9% |
| 3 | 431.97 | 74.8% | 74.7% |
| 4 | 557.22 | 76.5% | 76.2% |
| 5 | 859.89 | 83.4% | 83.3% |
| 6 | 709.60 | 84.3% | 84.3% |
| 7 | 479.98 | 85.1% | 85.0% |
| 8 | 434.06 | 85.7% | 85.7% |
| 9 | 394.40 | 86.3% | 86.1% |
| 10 | 878.68 | 86.7% | 86.7% |
| 11 | 427.80 | 87.2% | 87.1% |
| 12 | 559.30 | 87.6% | 87.6% |
| 13 | 488.33 | 88.1% | 88.1% |
| 14 | 436.15 | 88.4% | 88.4% |
| 15 | 876.59 | 88.8% | 88.7% |
| 16 | 484.16 | 88.9% | 88.9% |
| 17 | 402.75 | 89.2% | 89.1% |
| 18 | 425.71 | 89.3% | 89.3% |
| 19 | 880.76 | 89.4% | 89.4% |
| 20 | 423.62 | 89.6% | 89.5% |
| 21 | 396.49 | 89.8% | 89.7% |
| 22 | 486.25 | 89.9% | 89.8% |
| 23 | 893.29 | 90.0% | 89.9% |
| 24 | 870.33 | 90.1% | 90.0% |

Branch 2: "Y" versus "GNN+GNF"

| Selection order | Wavelength | Calibration | Cross-validation |
|---|---|---|---|
| 1 | 431.97 | 86.4% | 86.4% |
| 2 | 429.89 | 87.0% | 87.0% |
| 3 | 866.15 | 88.9% | 88.1% |
| 4 | 559.30 | 90.4% | 89.8% |
| 5 | 868.24 | 90.7% | 90.3% |
| 6 | 542.61 | 91.1% | 90.7% |
| 7 | 557.22 | 91.4% | 91.0% |
| 8 | 434.06 | 91.6% | 91.3% |
| 9 | 509.21 | 91.8% | 91.6% |
| 10 | 413.19 | 92.0% | 91.8% |
| 11 | 427.80 | 92.1% | 92.0% |
| 12 | 561.39 | 92.2% | 92.1% |
| 13 | 409.01 | 92.4% | 92.2% |
| 14 | 400.66 | 92.6% | 92.4% |
| 15 | 544.69 | 92.7% | 92.5% |
| 16 | 893.29 | 92.8% | 92.6% |
| 17 | 734.65 | 93.1% | 92.7% |
| 18 | 657.41 | 93.4% | 93.1% |
| 19 | 436.15 | 93.5% | 93.3% |
| 20 | 889.11 | 93.7% | 93.4% |
| 21 | 743.00 | 93.8% | 93.5% |
| 22 | 820.23 | 93.8% | 93.6% |
| 23 | 732.56 | 94.0% | 92.7% |
| 24 | 659.50 | 94.1% | 93.8% |

Branch 3: "GNF" versus "GNN"

| Selection order | Wavelength | Calibration | Cross-validation |
|---|---|---|---|
| 1 | 398.57 | 58.5% | 58.3% |
| 2 | 396.49 | 60.4% | 60.6% |
| 3 | 400.66 | 61.9% | 61.8% |
| 4 | 394.40 | 62.7% | 62.6% |
| 5 | 434.60 | 63.0% | 63.0% |
| 6 | 550.96 | 68.5% | 67.1% |
| 7 | 494.60 | 73.9% | 72.3% |
| 8 | 822.32 | 75.3% | 73.5% |
| 9 | 500.86 | 76.0% | 74.2% |
| 10 | 425.71 | 77.0% | 74.9% |
| 11 | 546.78 | 77.8% | 75.6% |
| 12 | 726.30 | 77.9% | 75.9% |
| 13 | 655.33 | 78.6% | 76.6% |
| 14 | 626.10 | 78.8% | 77.2% |
| 15 | 826.49 | 79.1% | 77.4% |
| 16 | 505.03 | 79.5% | 77.8% |
| 17 | 874.50 | 79.5% | 78.0% |
| 18 | 634.45 | 79.7% | 78.0% |
| 19 | 657.41 | 79.8% | 78.4% |
| 20 | 649.06 | 79.9% | 78.5% |
| 21 | 818.14 | 80.2% | 78.7% |
| 22 | 847.37 | 80.2% | 78.9% |
| 23 | 667.85 | 80.3% | 79.0% |
| 24 | 786.83 | 80.2% | 79.1% |

Table 8

Figure 22

Table 10

| | 1st Branch: "Y" versus "GNF+GNN+GP" | | | | 2nd Branch: "GP" versus "GNN+GNF" | | | | 3rd Branch: "GNF" versus "GNN" | | |
|---|---|---|---|---|---|---|---|---|---|---|---|
| | | BCR (in %) | | | | BCR (in %) | | | | BCR (in %) | |
| Selection order | Wavelength | Calibration | Cross-validation | Selection order | Wavelength | Calibration | Cross-validation | Selection order | Wavelength | Calibration | Cross-validation |
| 1 | 475.81 | 84.3% | 84.3% | 1 | 431.97 | 75.5% | 75.6% | 1 | 398.57 | 58.5% | 58.3% |
| 2 | 540.52 | 84.8% | 84.7% | 2 | 427.80 | 77.2% | 77.2% | 2 | 396.49 | 60.4% | 60.6% |
| 3 | 717.95 | 85.7% | 85.9% | 3 | 477.90 | 80.3% | 80.3% | 3 | 400.66 | 61.9% | 61.8% |
| 4 | 486.25 | 85.8% | 86.1% | 4 | 434.06 | 81.8% | 81.8% | 4 | 394.40 | 62.7% | 62.6% |
| 5 | 657.41 | 86.2% | 86.3% | 5 | 891.20 | 83.3% | 83.2% | 5 | 434.06 | 63.0% | 63.0% |
| 6 | 701.25 | 86.3% | 86.6% | 6 | 559.30 | 87.5% | 87.4% | 6 | 550.96 | 68.5% | 67.1% |
| 7 | 845.28 | 86.7% | 86.8% | 7 | 872.41 | 88.2% | 88.2% | 7 | 494.60 | 73.9% | 72.3% |
| 8 | 680.37 | 86.8% | 86.9% | 8 | 486.25 | 88.8% | 88.7% | 8 | 822.32 | 75.3% | 73.5% |
| 9 | 490.42 | 86.9% | 87.0% | 9 | 394.40 | 89.2% | 89.2% | 9 | 500.86 | 76.0% | 74.2% |
| 10 | 655.33 | 87.1% | 87.2% | 10 | 429.89 | 89.8% | 89.7% | 10 | 425.71 | 77.0% | 74.9% |
| 11 | 684.55 | 87.2% | 87.4% | 11 | 398.57 | 90.1% | 90.1% | 11 | 546.78 | 77.8% | 75.6% |
| 12 | 686.64 | 87.3% | 87.4% | 12 | 438.24 | 90.3% | 90.3% | 12 | 726.30 | 77.9% | 75.9% |
| 13 | 659.50 | 87.5% | 87.5% | 13 | 880.76 | 90.5% | 90.5% | 13 | 655.33 | 78.6% | 76.6% |
| 14 | 803.53 | 87.6% | 87.7% | 14 | 465.37 | 90.7% | 90.7% | 14 | 626.10 | 78.8% | 77.2% |
| 15 | 728.38 | 87.6% | 87.7% | 15 | 396.49 | 90.9% | 90.9% | 15 | 826.49 | 79.1% | 77.4% |
| 16 | 682.46 | 87.7% | 87.8% | 16 | 517.56 | 91.1% | 91.0% | 16 | 505.03 | 79.5% | 77.8% |
| 17 | 582.27 | 87.7% | 87.9% | 17 | 557.22 | 91.3% | 91.3% | 17 | 874.50 | 79.5% | 78.0% |
| 18 | 546.78 | 87.8% | 87.9% | 18 | 406.92 | 91.5% | 91.5% | 18 | 634.45 | 79.7% | 78.0% |
| 19 | 651.15 | 87.8% | 88.0% | 19 | 421.54 | 91.6% | 91.6% | 19 | 657.41 | 79.8% | 78.4% |
| 20 | 661.59 | 88.0% | 88.1% | 20 | 436.15 | 91.8% | 91.7% | 20 | 649.06 | 79.9% | 78.5% |
| 21 | 571.83 | 88.0% | 88.1% | 21 | 511.29 | 91.9% | 91.9% | 21 | 818.14 | 80.2% | 78.7% |
| 22 | 454.93 | 88.0% | 88.1% | 22 | 882.85 | 92.1% | 92.0% | 22 | 847.37 | 80.2% | 78.9% |
| 23 | 617.75 | 88.0% | 88.1% | 23 | 425.71 | 92.1% | 92.1% | 23 | 667.85 | 80.3% | 79.0% |
| 24 | 400.66 | 88.0% | 88.2% | 24 | 423.62 | 92.3% | 92.3% | 24 | 786.83 | 80.2% | 79.1% |

Figure 23

METHOD AND SYSTEM FOR IDENTIFYING THE GRAM TYPE OF A BACTERIUM

FIELD OF THE INVENTION

The invention relates to the field of microbiological analysis, and in particular the characterization of microorganisms, especially the identification of yeasts and bacteria and within the framework of the latter the identification of their Gram type and their fermentative or non-fermentative character.

Advantageously, the invention applies to the analysis of a hyperspectral or multispectral image of a bacterial or yeast colony grown in a non-chromogenic, non-fluorogenic and dye-free nutrient medium.

PRIOR ART

In the field of pathogenic microorganisms, the characterization of a microorganism preferably consists of identifying its species and its susceptibility to an antimicrobial agent, (or "antibiogram"), in order to determine a treatment for the patient infected by this microorganism. To do this, a complex microbiological process is usually carried out in the laboratory, a process that usually requires prior knowledge of other properties of the microorganism, including its kingdom (e.g. yeast or bacteria), and in the bacterial context its Gram type or its fermentative or non-fermentative character. Indeed, this information makes it possible to choose a culture medium or a type of antimicrobial agent adapted to the microorganism in order to ultimately determine its species or its antibiogram. For example, the choice of an API® microorganism identification gallery marketed by the applicant is based on knowledge of the kingdom of the microorganism (e.g. yeast vs. bacteria) or the Gram type of the bacterial strain to be identified. Similarly, the determination of the antibiogram of a bacterial strain by the Vitek® 2 system marketed by the applicant is based on the choice of a card according to the Gram type and the fermentative or non-fermentative character of said strain. It is also possible to cite the identification by MALDI-TOF mass spectrometry using a different matrix depending on whether the microorganism to be identified is a yeast or a bacterium. Knowing this information as early as possible enables the optimization of the microbiological process, in particular by accelerating the process or reducing the number of consumables used.

Knowledge of these properties also helps to reduce false positive identification of bacterial strains. As an example, in the context of the ChomID® Elite Medium marketed by the Applicant, knowledge of the fermentative character of the bacterial strain tested strengthens the identification of salmonella. In particular, a salmonella, a fermenting bacterium, and a *Pseudomonas*, a non-fermentative bacterium, both cause the chromogenic substrate to be vitiated. Knowing whether the bacterium is non-fermentative makes it possible to simply rule out the salmonella without additional microbiological testing.

In addition to characterizing a microorganism to guide the microbiological process in the laboratory, this information also has clinical utility. In particular, the Gram classification of a bacterial strain makes it possible to characterize its wall, for example its percentage of peptidoglycan, and is used in the taxonomy of bacteria or to evaluate as a first approximation their sensitivity to antibiotics. There are two types of bacteria, namely Gram-"positive" and Gram-"negative" bacteria. Similarly, it is observed that non-fermentative bacteria, i.e. bacteria unable to catabolize glucose, occupy a special place in pathogenic bacteria. Indeed, they have a high level of natural resistance to antibiotics and are involved in many nosocomial infections. Examples include *Pseudomonas aeruginosa* and *Acinetobacter*. Knowing quickly the fermentative or non-fermentative nature of a bacterium thus makes it possible to direct first-line antibiotic therapy more effectively and slow the spread of multidrug resistant strains.

Historically, each of the properties mentioned above (kingdom, Gram and fermentative) is obtained by a dedicated technique. For example, the Gram type of a bacterial strain was determined by a manual technique called "Gram staining", which includes a large number of manual steps (fixing, staining, application of mordant, washing, overstaining . . . ) and is therefore long to implement. Various techniques have therefore been developed to automate the detection of the Gram type of bacteria, in particular to process a large number of samples. However, these techniques essentially continue to modify the electromagnetic response of the bacteria or their environment to make their Gram type easily observable. In particular, a first type of technique consists in automating the staining of the bacterial membrane on microscope slides, but the final decision on the Gram type is always made by a technician observing the slides under the microscope. This type of technique is therefore not fully automated, and moreover difficult to automate. Indeed, the difference in color between Gram-positive and Gram-negative bacteria can be subtle, which explains why the intervention of a laboratory technician is still necessary. A second type of technique consists in putting bacteria in the presence of a substrate that degrades by an enzymatic reaction initiated by the peptidoglycans of the bacteria's membranes. This reaction produces chromophores or fluorophores whose concentration is an indication of Gram type. This is usually referred to as chromogenic or fluorogenic "labeling" of bacteria. While this type of prior art technique can be automated, for example by measuring the light intensity of chromophores/fluorophores using a suitable device (e.g. spectrometer/fluorometer) and then comparing the measured intensity with predefined threshold values by computer, it nevertheless requires the design of special, often expensive chromophore or fluorogenic substrates. Moreover, whatever the technique used, the bacteria undergo a modification of their natural state (e.g. they contain dyes, have fixed chromogenic or fluorescent markers, etc.) and therefore can no longer be used for subsequent characterization tests (e.g. the determination of an antibiogram).

For the determination of the fermentative or non-fermentative character of a bacterium, it is usually implemented by the use of chromogenic media which change color depending on the fermentative or non-fermentative character of the bacterial strain tested. For example, the "Kligler-Hajna" test consists of growing the strain on a culture medium containing a colorimetric indicator that changes color according to the pH, lactose, glucose, thiosulfate and ferrous ions. This medium detects the fermentative character of the bacterium by the catabolism of glucose, which results in a colorimetric shift of the pH indicator. There are also media for testing the activity of tributyrin esterase of the bacterial strain that allow the characterization of Gram-negative and non-fermentative bacteria.

DISCLOSURE OF THE INVENTION

The purpose of the present invention is to provide a process for determining the Gram type and the fermentative character of a strain of bacteria which is automatic and which does not require labelling or staining of the bacteria or its culture medium to determine these characteristics.

For this purpose, the invention relates to a process for detecting the Gram type and the fermentative character of a bacterial strain, comprising:
- illuminating in the wavelength range 390 nm-900 nm at least one bacterium of said strain having a natural electromagnetic response in said range;
- acquiring, within said range, a light intensity reflected from or transmitted through said illuminated bacterium; and
- determining the Gram type and the fermentative character of the bacterial strain as a function of the acquired light intensity in said range.

"Natural electromagnetic" response means that the bacteria are not modified with the aid of elements (dye, chromogen, fluorogen, etc.) that alter their electromagnetic response to illumination at least in the wavelength range of interest. For example, a colony of the strain is grown in a non-chromogenic, non-fluorescent nutrient medium and the illumination/acquisition is done directly on the colony still present in its medium.

In other words, the inventors discovered that in the wavelength range 390 nm-900 nm a bacterium "naturally" has an electromagnetic signature characteristic of its Gram type and of its fermentative or non-fermentative character. The process according to the invention thus consists of measuring this signature and then extracting from it the Gram type and the fermentative character of the bacterium. Thus, it is not necessary to use a chromogenic or fluorogenic substrate or dyes. Moreover, the process according to the invention is fast in that it consists of illuminating, measuring a spectrum and performing a processing, including computer processing, of this spectrum. In particular, thanks to the invention it is possible to determine, using the 390-900 nm range, whether the bacterial strain is Gram-positive or Gram-negative and fermentative or Gram-negative and non-fermentative, knowledge of this information making it possible, for example, to optimize a laboratory microbiological process as described above.

It should be noted that the determination of the Gram type and the fermentative character is carried out directly from the acquired light intensity, without requiring the prior determination of the species or genus or family of the bacterial strain. In particular, the process of the invention differs from a process according to which the species of the bacterial strain is first identified and then the Gram type and the fermentative character are deduced from the knowledge of the species. Not having to identify the bacterial strain at the species level has the advantage of greatly simplifying the model for predicting the Gram type and the fermentative character. Indeed, identification at the species level requires a prediction model with a very high number of classes. For example, in the case of urinary tract infection it is estimated that infection is caused in 99% of cases by a bacterial strain among about fifty bacterial species. Identification at the species level therefore requires a prediction at about fifty classes. According to the invention, the prediction model can be limited to four classes.

Advantageously, the process is applied to a Petri dish comprising an agar nutrient medium on which colonies of microorganisms have grown. For example, the nutrient medium is inoculated with a biological sample containing, or suspected to contain, yeasts or bacteria, e.g. urine, and then cultured to grow the colonies. As soon as a colony is detected on the nutrient medium, it is characterized according to the process of the invention. Thus, the process does not require any material transfer or reagent addition following the inoculation of the nutrient medium. The detection of a colony is, for example, carried out automatically by taking images of the Petri dish at regular intervals and implementing a colony detection algorithm.

Advantageously, the process according to the invention is not based on the analysis of the autofluorescence of the bacterial strain but on the analysis of the reflectance or absorbance of said strain. In particular, the illumination is generally too intense for the autofluorescence to be observable on a hyperspectral or multispectral image.

The invention also relates to a process for producing an antibiogram of a bacterial strain of an antibiotic comprising:
- determination of the Gram type and the fermentative character of the bacterial strain;
- providing at least one sample comprising the bacterial strain, a culture medium and a concentration of an antibiotic as a function of the Gram type and the selected fermentative character; and
- determining the sensitivity of the bacterial strain to the antibiotic as a function of the growth of said strain in the sample, process wherein the determination of the Gram type and the fermentative character of the bacterial strain is carried out according to a process of the aforementioned type.

The invention also relates to a process for identifying a bacterial strain to an antibiotic comprising:
- determination of the Gram type and the fermentative character of the bacterial strain;
- selection of at least one colorimetric medium according to the Gram type and the selected fermentative character; and
- culturing the bacterial strain in said medium, process wherein the determination of the Gram type and the fermentative character of the bacterial strain is carried out according to a process of the aforementioned type.

The invention also relates to a system for implementing the process just described. In particular, the invention relates to a detection system for detecting the Gram type and the fermentative character of a bacterial strain, comprising:
- an illumination configured to illuminate, in the wavelength range 390 nm-900 nm, at least one bacterium of the strain;
- a sensor configured to acquire, in the 390 nm-900 nm range, a light intensity reflected from or transmitted through said illuminated bacterium; and
- a computer unit configured to determine the Gram type and the fermentative character of the bacterial strain as a function of the acquired light intensity in the range 390 nm-900 nm.

According to an embodiment, the system is configured to illuminate, and acquire the image of, a sample comprising a colony of bacteria of said strain and nutrient medium on which said colony has grown, in particular a Petri dish.

The invention also relates to a process for calibrating a system for carrying out a process according to the invention, the system comprising:
- an illumination configured to illuminate, in the wavelength range 390 nm-900 nm, at least one bacterium of the strain;
- a sensor configured to acquire, in the 390 nm-900 nm range, a light intensity reflected from or transmitted through said illuminated bacterium; and
- a computer unit comprising a computer memory capable of containing analysis instructions for the intensity acquired by the sensor and a microprocessor capable of executing the analysis instructions contained in the computer memory, the calibration process comprising the steps of:

building a training database comprising light intensities in the range 390 nm-900 nm of bacterial strains illuminated in said range, said strains being associated with different Gram types and different fermentative characters;

implementing by computer the machine learning of a model for predicting the Gram type and the fermentative character of a bacterial strain based on said database; and storage, in the system's computer memory, of analysis instructions for the implementation of the learned prediction model.

The invention also relates to a therapeutic process comprising:

taking a sample from a patient suspected of having a bacterial infection;

detecting one or more bacterial strains present in the sample, advantageously by inoculating an agar culture medium with the sample, culturing said inoculated medium to grow bacterial colonies and detecting one or more grown bacterial colonies;

detecting the Gram type or the fermentative character of the bacterial strain(s) detected by a process of the abovementioned type;

selecting one or more antibiotics based on the Gram type and the fermentative character detected; and administering the selected antibiotic(s) to the patient.

BRIEF DESCRIPTION OF THE FIGURES

The invention will be better understood upon reading the description which follows, given solely by way of example, and made in relation to the appended drawings, in which identical reference symbols designate identical or similar elements, and in which

FIG. 8 is a table describing the bacterial and yeast species used for learning predictive models for classes Y, GP, GNF, GNN;

FIGS. 9 and 10 are tables, respectively for the COS and TSA media, describing the number of pixels, and thus spectra, used for calibration and cross-validation of prediction models;

FIG. 11 is a graph illustrating the calculation of a weighted prediction rate, or balanced classification rate.

FIG. 21 summarizes BCRs and relationships for solving an optimization problem in models of FIG. 7C and obtained using the step-forward approach in FIG. 4;

FIG. 22 summarizes BCRs and relationships for solving an optimization problem in models of FIG. 7C and obtained using the step-forward approach in FIG. 5;

FIG. 23 summarizes BCRs and relationships for solving an optimization problem in models of FIG. 7B and obtained using the step-forward approach in FIG. 4.

DETAILED DESCRIPTION OF THE INVENTION

Hereinafter, the notation $A_{i,j}$ refers to the element in the $i^{th}$ row and $i^{th}$ column of the matrix A.

Figure 1:
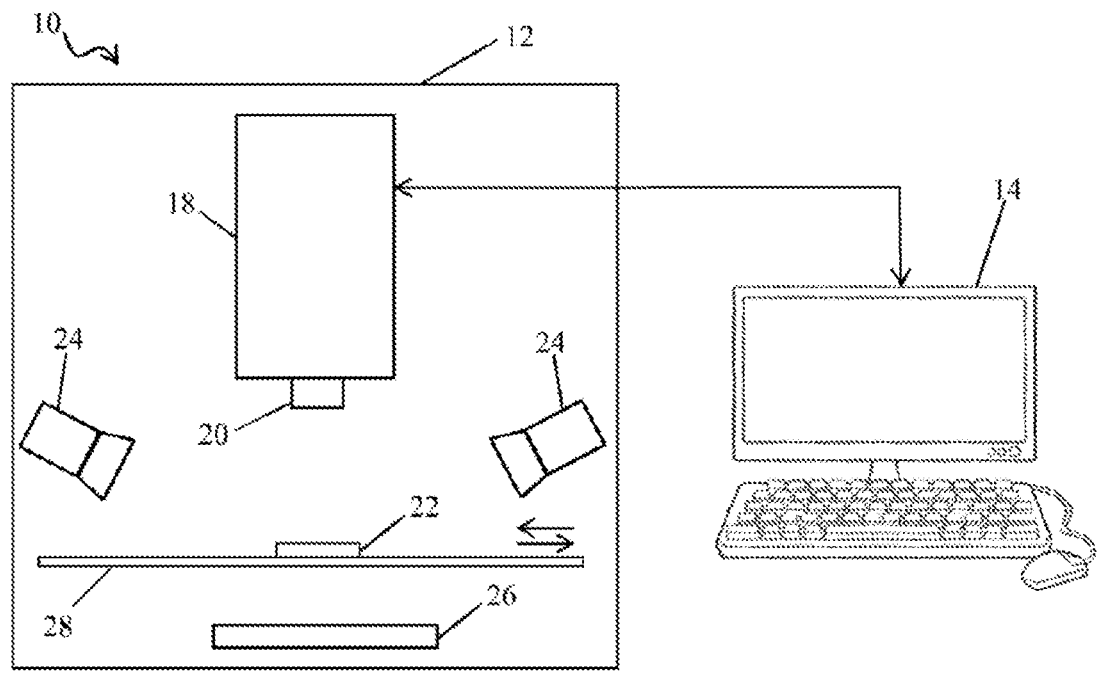
FIG. 1 is a schematic view of a hyperspectral system according to the invention.

Referring to FIG. 1, a hyperspectral system 10 for characterizing yeast or bacterial colonies grown on agar cast in a Petri dish comprises:

a hyperspectral image acquisition device 12; and a data-processing unit 14 connected (e.g. by a wired or wireless link) to the device 12 for its control and for receiving and processing images acquired by the device 12.

The device 12, for example a reference hyperspectral imaging system "Pika II" from Resonon, Mont. USA, includes:

a so-called "hyperspectral" camera 18, consisting of a digital sensor comprising an array of elementary sensors, for example a CCD or CMOS digital sensor, sensitive in the wavelength range $[\lambda_{min}; \lambda max]=[390; 900]$ nanometers, and a light dispersive element or spectrograph to select a wavelength to be acquired by the sensor;

a lens 20 to focus on the digital sensor of the camera 18, the optical image of a Petri dish 22, of which a hyperspectral image is sought to be acquired;

a front illumination 24, e.g. consisting of one or more allogenic lamps, e.g. 2 or 4 lamps, capable of emitting light within the range of $[\lambda_{min}; \lambda_{max}]$ and to achieve uniform front illumination of the Petri dish 22. For example, the lights are white light lamps;

a rear illumination 26, for example consisting of a white light LED array, to provide uniform rear illumination of the Petri dish 22 in the range of [$\lambda_{min}$; $\lambda_{max}$] and a carriage 28 on which rests the Petri dish 22 and allowing the latter to scroll in front of the lens 20 in order to obtain a whole image of the Petri dish 22 by scanning.

Illumination is thus provided across the entire range [$\lambda_{min}$; $\lambda_{max}$]

The device 12 is, for example, configured to acquire the image of a 90 millimeter by 90 millimeter region with a sampling step of 160 micrometers (spatial resolution estimated at 300 micrometers) and with a spectral resolution of 1.7 nanometers over the range [$\lambda_{min}$; $\lambda_{max}$].

The device 12 thus produces a digital image HSI of light reflected by the Petri dish, having N rows and M columns, the Petri dish 22 being preferably open (i.e. without its cover):

$$HSI(\lambda) = \begin{pmatrix} Rad_{1,1}(\lambda) & \ldots & Rad_{1,j}(\lambda) & \ldots & Rad_{1,M}(\lambda) \\ \vdots & \ddots & \vdots & & \vdots \\ Rad_{i,1}(\lambda) & \ldots & Rad_{i,j}(\lambda) & \ldots & Rad_{i,M}(\lambda) \\ \vdots & & \vdots & \ddots & \vdots \\ Rad_{N,1}(\lambda) & \ldots & Rad_{N,j}(\lambda) & \ldots & Rad_{N,M}(\lambda) \end{pmatrix} \quad (1)$$

The radiance of a pixel, commonly referred to as "light intensity", corresponds here to the amount of light incident on the surface of the corresponding elementary sensitive site of the sensor of the camera 18 during the exposure time, as is known per se from the field of digital photography for example.

Each pixel $Rad_{i,j}(\lambda)$ consists of a digital spectrum of the radiance of the dish 22 corresponding to the pixel at different wavelengths [$\lambda_{min}$; $\lambda_{max}$], the numerical spectrum being expressed according to the relationship:

$$\forall (i, j) \in [1, N] \times [1, M]: Rad_{i,j}(\lambda) = \begin{pmatrix} Rad_{i,j}(\lambda_{min}) \\ Rad_{i,j}(\lambda_{min} + \Delta\lambda) \\ Rad_{i,j}(\lambda_{min} + 2 \times \Delta\lambda) \\ \vdots \\ Rad_{i,j}(\lambda_{min} + p \times \Delta\lambda) \\ \vdots \\ Rad_{i,j}(\lambda_{max}) \end{pmatrix} \quad (2)$$

where $\Delta\lambda$ is the spectral resolution and p is a positive integer belonging to $$\left[0, P = \frac{\lambda_{max} - \lambda_{min}}{\Delta\lambda}\right].$$

Acquisition wavelengths $\lambda_{min}$ p×$\Delta\lambda$ are commonly referred to as "channels".

The data-processing unit 14 is, for example, a personal computer, a tablet, a smartphone, a server, a supercomputer, or more generally any system based on microprocessor(s), in particular digital signal processors (DSPs), based on FPGA-type circuits, based on circuits combining these types of technology, etc., configured to implement processing of images HSI produced by the acquisition device 12. The unit 14 is in particular provided with all the memories (RAM, ROM, cache, mass memory, . . . ) for storing the images produced by the device 12, with computer instructions for carrying out the process according to the invention, with parameters useful for this implementation and for storing the results of the intermediate and final calculations. The unit 14 optionally includes a display screen for the visualization of the final result of the characterization of the colonies, in particular the determination of the Gram type and/or the fermentative character, and/or the bacterial or yeast character of the colonies studied. Although only one processing unit is described, the invention obviously applies to processing carried out by several processing units (e.g. a unit on board camera 18 for implementing pre-processing of the images HSI and a unit external to the device 12 for implementing the rest of the processing). In addition, the system can be completed by an interface allowing the entry into the unit 14 of data relating to the sample, in particular the type of culture medium used when the prediction depends on the medium, e.g. by means of a keyboard/mouse and a drop-down menu available to the operator, a barcode/QR code reader reading a barcode/QR code present on the Petri dish and including information on the medium, etc.

The hyperspectral system in FIG. 1 has the advantage of being agile in terms of acquisition wavelengths because it can adapt to different colony class prediction models and use a large number of spectral channels to increase the accuracy of the prediction. However, in addition to a high price, such a system is generally less spatially resolved than a conventional CMOS or CCD camera whose only purpose is to acquire an image of the intensity of the light incident on its sensor.

Figure 2:
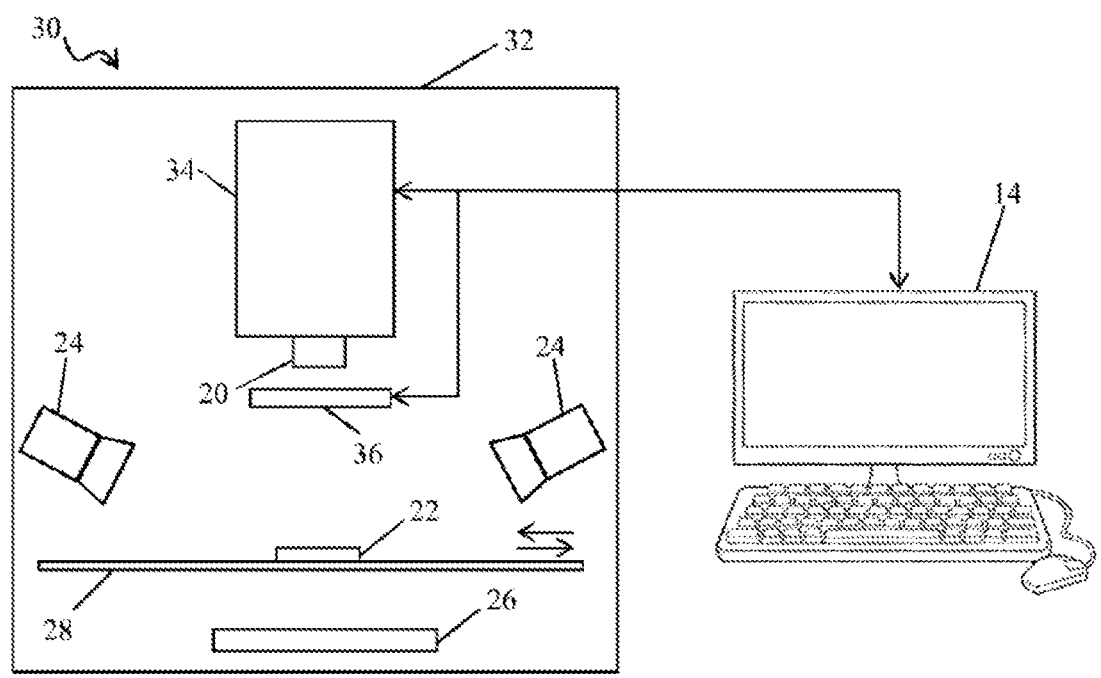
FIG. 2 is a schematic view of a multispectral system according to the invention.
Figure 3:
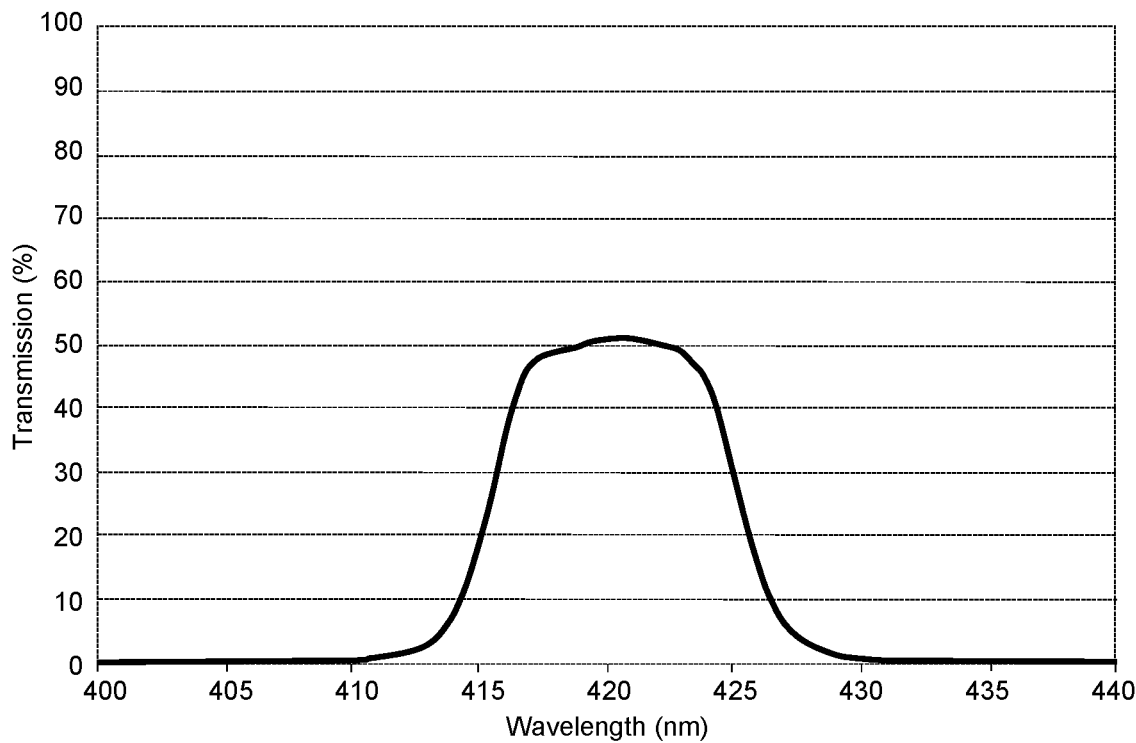
FIG. 3 is an example of the transmission spectrum of a bandpass filter used in the system of FIG. 2.

Referring to FIG. 2, a multispectral system 32 differs from the hyperspectral system 10 by the camera 32, advantageously a CMOS or CCD camera with high spatial resolution, coupled with a set of spectral filters 36, for example arranged in front of the lens 20 between the lens 20 and the sensor of the camera 32. The set of filters 36 consists of a number $N_F$ of separate bandpass filters, each configured to transmit only light in a range of [$\lambda_1$; $\lambda_2$] of the range [$\lambda_{min}$; $\lambda_{max}$] with a full width half maximum (FWHM) less than or equal to 50 nm, and preferably less than or equal to 20 nm. The transmission spectrum of such a filter, e.g. an Edmund Optics filter centered at 420 nm, is shown in FIG. 3. The assembly 36 is, for example, a filter wheel which can accommodate up to 24 different filters, driven by the unit 14 which operates it to scroll the filters in front of the camera and to control an image capture for each of them.

A multispectral image HSI($\lambda$) is thus acquired, each pixel $Rad_{i,j}(\lambda)$ of which consists of a digital spectrum of the radiance of the dish 22 corresponding to the pixel in the different spectral bands filtered by the assembly 36, the digital spectrum being expressed according to the relationship:

$$\forall (i, j) \in [1, N] \times [1, M]: Rad_{i,j}(\lambda) = \begin{pmatrix} Rad_{i,j}(\lambda_1) \\ Rad_{i,j}(\lambda_2) \\ \vdots \\ Rad_{i,j}(\lambda_{N_F}) \end{pmatrix} \quad (3)$$

Where $\lambda_1, \lambda_2, \ldots, \lambda_{N_F}$ are respectively the center wavelengths of the spectral filters of the assembly 36.

Figure 4:
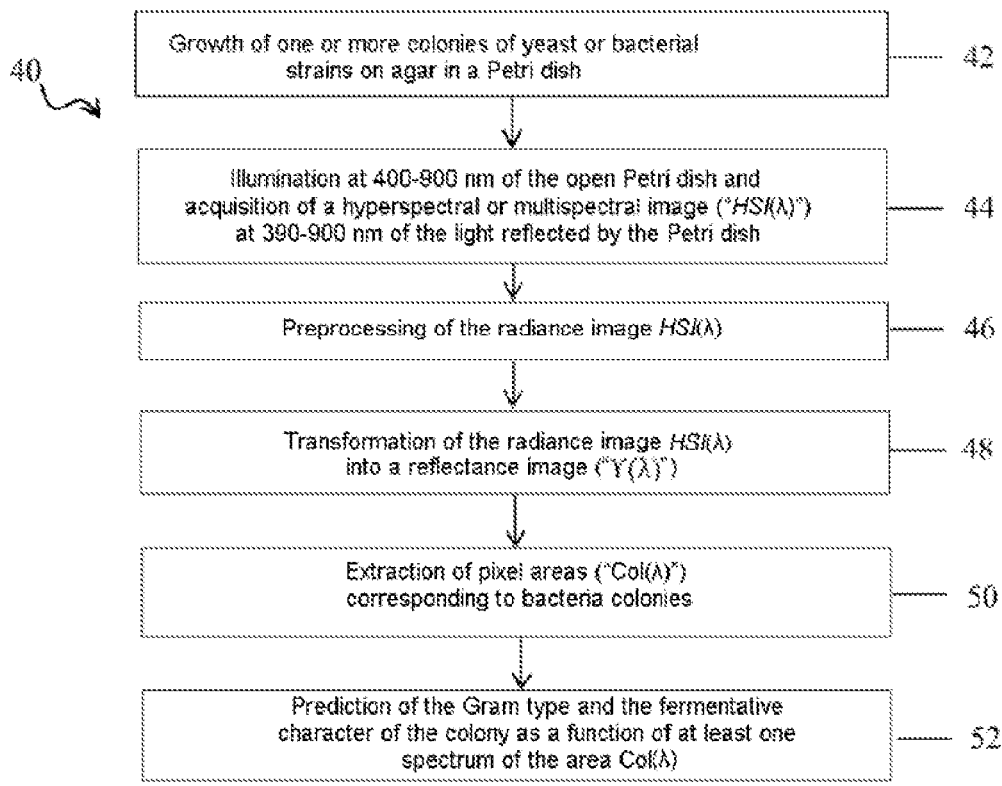
FIG. 4 is a flowchart of a prediction process for classes Y, GP, GNF, GNN implemented using the system of FIG. 1 or FIG. 2.

A process 40 for characterizing microorganisms contained in a biological sample (e.g. urine, blood, bronchoalveolar sampling, etc.) using the system just described is now detailed in relation to the flowchart in FIG. 4. In particular, this process is advantageously applied within the framework of a more global process for identifying the microorganisms contained in said sample by means of MALDI-TOF mass spectrometry (e.g. Vitek® MS marketed by the Applicant) and an antibiogram of said microorganisms (e.g. by means of the Vitek® 2 platform marketed by the Applicant). As is known per se, each of these techniques requires the choice of specific media and/or reagents and/or consumables depending on the type of microorganism. By way of example, the identification of yeasts by MALDI-TOF mass spectrometry advantageously involves the use of formic acid in the matrix used in this type of technology.

Similarly, the choice of the Vitek® 2 platform card (card comprising a growth medium and one or more antimicrobials tested during the antibiotic susceptibility test) depends on the bacterial nature of the microorganism tested. In particular, Gram-negative and fermentative bacteria require a special card to perform their antibiogram.

In an advantageous way, the characterization process 40 described below allows, from the first growth on a Petri dish, to obtain the necessary information on the microorganisms for the continuation of the microbiological process, in particular whether a colony that has grown is a yeast ("Y") or a bacterium, and in the case of a bacterium, whether that bacterium is Gram-positive ("GP") or Gram-negative ("GN"), and in the case of Gram-negative bacteria, whether that bacterium is fermentative ("GNF") or non-fermentative ("GNN"). The process thus makes it possible to predict the class of a microorganism, to have the class Y, GP, GNF or GNN.

In a first step 42 of the process, a Petri dish is inoculated with a biological sample, e.g. taken from a patient, to grow yeast or bacterial colonies on the surface of a nutrient medium, or "culture", deposited in the Petri dish. The main purpose of the nutrient medium is to grow said colony, and optionally to enhance the accuracy of the characterization by limiting light disturbance. Preferably concerning a Gram type detection according to the reflected light intensity, the nutritive medium is opaque, which increases the degree of precision of the detection. In particular, the opaque medium has a reflectance factor p less than or equal to 10%, and preferably less than or equal to 5%, and even more preferentially less than or equal to 1%. For example, the culture medium a so-called "CPSO" agar ("CPS" agar comprising $SiO_2$ to opacify the medium), a so-called "columbia" agar ("CNA" agar), Columbia agar with 5% sheep blood ("COS" agar), a Man, Rogosa, Sharpe ("MRSM") agar, chocolate ("PVX") agar, Tryptone-Soy agar ("TSA"), etc.

This type of colony growth is classic and will not be described in more detail hereinbelow. It can advantageously be carried out manually by an operator or automatically using an automatic inoculating machine in a manner known per se. Advantageously, the preparation is carried out in such a way that the colonies, on the basis of which the characterization of the microorganism is carried out, are spaced apart from each other and so that the surface area of a colony corresponds to a plurality of pixels in the image acquired by the device 12. This makes it possible in particular to facilitate their subsequent identification in the acquired image, and thus their segmentation by means of an image processing algorithm or their extraction in the image by a user.

Once the colony growth is finished, for example after a period of 24 h, 36 h or 48 h, the Petri dish is preferably opened, placed on the carriage 28, the illumination 24 and 26 are switched on and at least one hyperspectral (respectively multispectral) image HSI of the Petri dish is acquired, in 44, with the aid of the acquisition device 12 (respectively 32) and stored in the processing unit 14, which implements a computer processing to determine the type of microorganism constituting the colony from the acquired images.

The unit 14 optionally starts, in 46, with a noise pre-processing, consisting of one of the following types of processing or any combination thereof:
 a. a correction of the camera sensor noise, in particular its offset, spatial noise, etc., in a manner known per se;
 b. processing of parasitic reflections, especially specular reflections forming "highlights" in the image HSI. For example, thresholding implemented to eliminate pixels with values greater than a predetermined threshold, e.g. greater than or equal to two thirds of the maximum value that the pixels can take (i.e. greater than or equal to 170 in the case of pixels encoded on 8 bits between 0 and 255);
 c. ratiometric processing to attenuate variations in the images caused by external fluctuations such as variations in illumination, by dividing the image HSI by a reflected light intensity at a wavelength that is invariant with the type of bacteria and the type of agar used;
 d. if multiple images HSI have been acquired, searching for and eliminating outliers and/or the average of the acquired images.

Advantageously, the processing continues, in 48, by transforming the pre-processed image HSI, which stores radiance values at different wavelengths, into a hyperspectral or multispectral reflectance image in order to extract the signal generated by the Petri dish alone. This makes it possible in particular to filter the fluctuations of the emission spectrum of the illumination sources 24, 26. For example, a flat field correction (FFC) is implemented to obtain the reflectance, which also has the advantage of correcting the sensor's response dispersions from pixel to pixel (dark current dispersion, gain dispersion, etc.).

In the context of a hyperspectral image, this transformation is for example a correction according to the relationships:

$$\forall (i,j) \in [1,N] \times [1,M], \forall p \in [0,P]: \Upsilon_{i,j}(\lambda_{min} + p \times \Delta\lambda) = \quad (4)$$

$$\frac{\mathrm{Rad}_{i,j}(\lambda_{min} + p \times \Delta\lambda) - B_{i,j}(\lambda_{min} + p \times \Delta\lambda)}{W_{i,j}(\lambda_{min} + p \times \Delta\lambda) - B_{i,j}(\lambda_{min} + p \times \Delta\lambda)} \times m(\lambda_{min} + p \times \Delta\lambda)$$

where $\Gamma(\lambda)$ is a reflectance image, W is a hyperspectral image stored in the unit 14 of a neutral object of high reflectance and illuminated by the illumination 24, 26, for example a sheet of uniform reflectance greater than 90% (e.g. a so-called "white" sheet or with a grey chart less than 10%), and B is a hyperspectral image stored in the unit 14 of a neutral object of low reflectance, such as the image of a black cap blocking the lens 20 and $m(\lambda_{min}+p\times\Delta\lambda)=1$ or equal to the average of the matrix $W(\lambda_{min}+p\times\Delta\lambda)-B(\lambda_{min}+p\times\Delta\lambda)$.

Similarly, in the context of a multispectral image, the transformation is for example a correction according to the relationship:

$$\forall (i,j) \in [1,N] \times [1,M], \forall n \in [1,N_f]: \quad (5)$$

$$\Upsilon_{i,j}(\lambda_n) = \frac{\mathrm{Rad}_{i,j}(\lambda_n) - B_{i,j}(\lambda_n)}{W_{i,j}(\lambda_n) - B_{i,j}(\lambda_n)} \times m(\lambda_n)$$

where W is a multispectral image stored in the unit 14 of a neutral object of high reflectance and illuminated by illumination 24, 26, for example a sheet of uniform reflectance greater than 90% (e.g. a so-called "white" sheet or with a grey scale less than 10%), and B is a multispectral image stored in the unit 14 of a neutral object of low reflectance, such as the image of a black cap blocking the lens 20 and $m(\lambda_n)=1$ or equal to the average of the matrix $W(\lambda_n)-B(\lambda_n)$. The unit 14 implements in 50, following step 38 or in parallel with the previous steps, an algorithm for identifying bacteria colonies, e.g. from the image $HSI(\lambda)$ or $Y(\lambda)$. Any standard pattern and object recognition algorithm can be used to extract an area of the image, called "Col($\lambda$)", corresponding to a colony. Alternatively, this selection is made manually by an operator who selects this field using the display screen and a pointing mechanism such as a mouse for example. As an example, the field Col($\lambda$) consists of a list of pixel coordinates belonging to the colony. The selected pixel areas are stored by the unit 14.

The process continues, in 52, by predicting the class Y, GP, GNF or GNN of the microorganism in the colony according to at least one spectrum of the zone Col($\lambda$) by applying predefined decision rules, variants of which are described below. In particular, this prediction is made on the basis of the spectrum $\Gamma_{i,j}(\lambda)$ of each pixel (i,j) of the area Col($\lambda$). For this purpose, a first prediction of the class is made for each pixel (i,j) of the area Col($\lambda$) and then a majority vote is implemented for the final prediction of the class. In a first variant, a simple majority vote is implemented, i.e. the class predicted on the largest number of pixels of the Col($\lambda$) is the class finally selected. In a second variant, in order to increase the certainty in the prediction of the class, a qualified vote is implemented, i.e. the class finally retained is the one predicted on more than X % of the number of pixels constituting the Col($\lambda$), with X strictly greater than 50%, and preferably greater than or equal to 70%. If no class meets this condition, the process returns an absence of class prediction. Of course, the class of the colony can be realized using a single value, for example the mean spectrum $\Gamma_{col}(\lambda)$ of the set $\{\Gamma_{i,j}(\lambda)\}_{(i,j)\in Col(\lambda)}$ of spectra of the area Col($\lambda$).

The class Y, GP, GNF or GNN of each colony by the unit 14 is achieved by applying predefined prediction rules, variants of which are described below. The predicted classes are stored in the unit 14 and/or displayed on a screen for the user. This prediction is also advantageously delivered to another microbial analysis instrument for a subsequent step of identification and/or antibiotic susceptibility testing of the microorganisms that formed the colonies.

Different prediction models of a class Y, GP, GNF or GNN as a function of a spectrum $\Gamma_{i,j}(\lambda)$ of a colony pixel will now be described, including prediction models based on supervised machine learning (SML). The SML tools used are first described in relation to FIG. 5 and then the prediction models are described below through their learning process illustrated in FIGS. 6 and 7.

A. SUPERVISED MACHINE LEARNING TOOLS

Regardless of the type of learning being considered, it begins with the creation of a learning database. For each Y, GP, GNF and GNN class, bacteria and yeasts are selected and each of them is seeded on an agar cast in a Petri dish, cultured for a predetermined time and a hyperspectral image of the dish is acquired with the system described in FIG. 1, and therefore under the same illumination conditions and in the wavelength range 390 nm-900 nm. The pixels of the colonies grown on the agar are extracted, for example as described in steps 46-50 of process 40, and their associated spectra stored in the training database. The training database thus includes four sets of spectra $\{\Gamma_m^Y(\lambda)\}$, $\{\Gamma_m^{GP}(\lambda)\}$, $\{\Gamma_m^{GNF}(\lambda)\}$, $\{\Gamma_m^{GNN}(\lambda)\}$ respectively associated with the classes Y, GP, GNF, GNN. Each of these sets is divided into two parts, a first part, called "calibration", being used for the training itself and a second part, called "cross-validation", being used to evaluate the performance of the calculated prediction models, as is known per se from the prior art.

According to a first special embodiment, computer-implemented learning, known as "step-forward", is used to learn prediction models. This type of learning is based on the step-by-step selection of the most discriminating spectral channels, so that it is intrinsically parsimonious and suitable for multispectral application as implemented by the system in FIG. 2.

Figure 5:
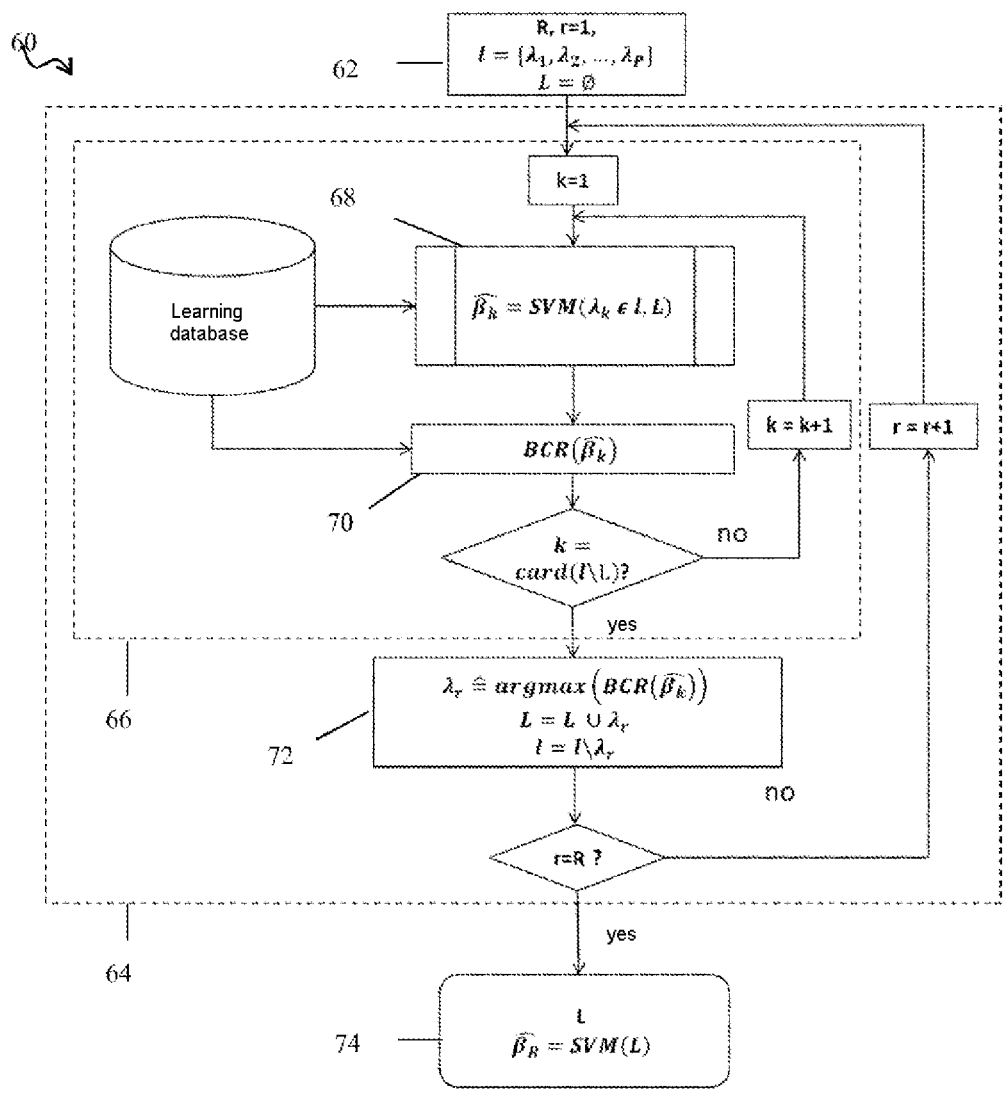
FIG. 5 is a flowchart of a process for selecting discriminating spectral channels using the step-forward approach.

Referring to FIG. 5, learning 60 starts with an initialization step 62 wherein a maximum number R of discriminating channels is selected, this number being between 1 and the number P of spectral channels of the hyperspectral camera used for spectrum acquisition. A list L of the selected discriminating channels is emptied and a list l of the candidate channels is initialized to the set $\{\lambda_1, \lambda_2, \ldots, \lambda_P\}$ of the hypespectral camera channels.

In a subsequent iterative step 64, the list l is filled step by step with the most discriminating R channels of the list L by implementing an iterative step 66. Specifically, for a given iteration r of step 64, step 66:

extract each channel $\lambda_k$ of the list l;

determine, in 68, for the extracted channel $\lambda_k$ and the channels $\{\lambda_1, \lambda_2, \ldots, \lambda_{r-1}\}$ from the L list, a prediction model $\widehat{\beta_k}$;

calculate, in 70, a performance criterion BCR ($\widehat{\beta_k}$) of the prediction model $\widehat{\beta_k}$, for example the rate of good classification of cross-validation spectra.

Step 64 then continues, in 72, with the identification of the prediction model giving the best performance criteria and consequently the identification of the channel $\lambda_r$ of the most discriminating list l in combination with the channels in the list L. In 74, the list L is then completed with the channel $\lambda_r$ and it is removed from the list l for the next iteration r+1 of step 64. Once the most discriminating R channels have been identified, the learning process then ends, in 74, by storing the list L and the prediction hyperplane ($\widehat{\beta_R}$, $\beta_0^{cl}$) associated with the latter, namely the last model identified in step 72.

Advantageously, the prediction models calculated in step 68 are of the support vector machine (SVM) type, "one against all", linear kernel and soft margin. This type of training consists in calculating, according to the calibration spectra, a hyperplane ($\widehat{\beta_k^{Cl}}$, $\beta_0^{cl}$) separating a class Cl (Cl=Y, GP, GNF or GNN) from the set $\overline{Cl}$ formed from one, two or three of the other classes, as described below. For example, the model is learned by solving an optimization problem according to the following relationships for an iteration k of step 66 and an iteration r of step 64:

$$\widehat{\beta_k^{Cl}} = \arg\min_{\beta,\xi_m}\left(\frac{1}{2}\|\beta\|^2 + C\sum_{m=1}^M \xi_m\right)$$

under the constraints:

$\forall m \in [1,M]: \xi_m \geq 0$ $\forall m \in [1,M]: q_m(\Gamma_m^{r,k}(\lambda)\cdot\beta + \beta_0^{cl}) \geq 1-\xi_m$ \hfill (6)

expressions wherein:

for a calibration spectrum $\Gamma_m(\lambda)$ belonging to the class Cl or to the set $\overline{Cl}$, $\Gamma_m^{r,k}(\lambda)$ is equal to the vector of the components of $\Gamma_m(\lambda)$ corresponding to the spectral channels in the list $L=\{_1, \lambda_2, \ldots, \lambda_{r-1}\}$ and the channel $\lambda_k$ extracted from the list 1 during the iteration k, preferably a vector whose components are ordered according to the value of the channels;

$\widehat{\beta_k^{Cl}}$ and $\beta$ are vectors of a dimension equal to the dimension of the spectra $\Gamma_m^{r,k}(\lambda)$ and therefore of a dimension equal to r, M is the number of calibration spectra $\Gamma_m(\lambda)$ belonging to the class Cl or to the set $\overline{Cl}$, numbered 1 through M, $\Gamma_m^{r,k}(\lambda)$. $\beta$ is the scalar product between the vector $\Gamma_m^{r,k}(\lambda)$ and the vector $\beta$, $\xi_m$ and $\beta_0^{cl}$ are scalars;

$q_m \in \{1, 1\}$ with $q_m=1$ if the $m^{th}$ learning spectrum is associated with the class Cl, and $q_m=-1$ if the $m^{th}$ spectrum is associated with the set $\overline{Cl}$ of the other classes; and C a predefined scalar.

The model predicting the membership to a class Cl of a one-pixel spectrum $Y_{i,j}(\lambda)$ is thus carried out according to the following steps:

spectrum transformation $Y_{i,j}(\lambda)$ in a vector $\Gamma_{i,j}^{r,k}(\lambda)$;

the calculation of a distance $S_{cl}=\Gamma_{i,j}^{r,k}(\lambda) \cdot \widehat{\beta_k} + \beta_0$ across the spectrum $\beta_{i,j}^{r,k}(\lambda)$ and the hyperplane $(\widehat{\beta_k^{Cl}}, \beta_0^{cl})$;

the application of a prediction rule of the class Cl as a function of the distance $S_{cl}$, for example, the spectrum belongs to the class Cl if the sign of $S_{cl}$ is positive, and overall $\overline{Cl}$ if that sign is negative.

According to a second embodiment, learning is not parsimonious and consists of using all channels at the same time, as the resulting prediction model is particularly well suited to a hyperspectral application using the system shown in FIG. 1. For example, this training is of the SVM type, "one against all", with a linear kernel and a flexible margin, and consists of calculating, as a function of the calibration spectra, a hyperplane$(\widehat{\beta^{Cl}}, \beta_0^{cl})$ separating a class Cl (Cl=Y, GP, GNF or GNN) from the set $\overline{Cl}$ formed from one, two or three of the other classes, by solving an optimization problem according to the relationship:

$$\widehat{\beta^{Cl}} = \arg\min_{\beta, \xi_m}\left(\frac{1}{2}\|\beta\|^2 + C\sum_{m=1}^{M}\xi_m\right)$$

under the constraints:

$\forall m \in [1,M]: \xi_m \geq 0$ $\forall m \in [1,M]: q_m(\Gamma_m(\lambda) \cdot \beta + \beta_0^{cl}) \geq 1-\xi_m$    (7)

expressions wherein:

$\Gamma_m(\lambda)$ is a calibration spectrum $\Gamma_m(\lambda)$ belonging to the class Cl or to the set $\overline{Cl}$;

$\widehat{\beta^{Cl}}$ and $\beta$ are vectors of a dimension equal to the dimension of the calibration spectra $\Gamma_m^{r,k}(\lambda)$, and therefore of dimension equal to P, M is the number of calibration spectra $\Gamma_m(\lambda)$ belonging to the class Cl or to the set $\overline{Cl}$, numbered 1 through M, $\Gamma_m(\lambda)$. $\beta$ is the scalar product between the vector $\Gamma_m(\lambda)$ and the vector $\beta$, $\xi_m$ and $\beta_0^{cl}$ are scalars;

$q_m \in \{-1, 1\}$ with $q_m=1$ if the $m^{th}$ learning spectrum is associated with the class Cl, and $q_m=-1$ if the $m^{th}$ spectrum is associated with the set $\overline{Cl}$ of the other classes; and C a predefined scalar.

The model predicting the membership to a class Cl of a spectrum of one pixel $\Gamma_{i,j}(\lambda)$ is thus carried out according to the following steps:

the calculation of a distance $S_{cl}=\Gamma_{i,j}(\lambda) \cdot \widehat{\beta^{Cl}} + \beta_0^{cl}$ between the spectrum $\Gamma_{i,j}(\lambda)$ and the hyperplane $(\widehat{\beta^{Cl}}, \beta_0^{cl})$;

the application of a prediction rule of the Cl class as a function of the distance $S_{cl}$, for example the spectrum belongs to the class Cl if the sign of $S_{cl}$ is positive, and to the set $\overline{Cl}$ if that sign is negative.

B. PROCESS FOR LEARNING PREDICTION MODELS

Figure 6:
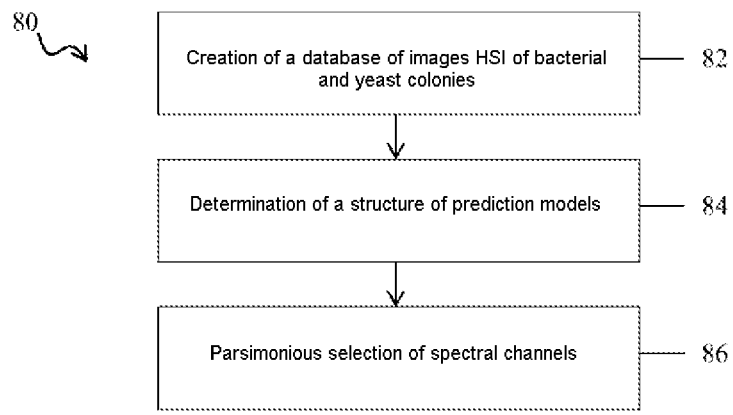
FIG. 6 is a flowchart of a process for learning prediction models for classes Y, GP, GNF, GNN.

Referring to FIG. 6, the learning process 80 for the prediction models starts with the establishment, in 82, of a learning database for the classes Y, GP, GNF and GNN, as described above. The process 80 continues, in 84, with the determination of a prediction model structure. In particular, two types of models are possible, as shown respectively in FIG. 7A and in FIGS. 6B and 6C.

Figure 7A:
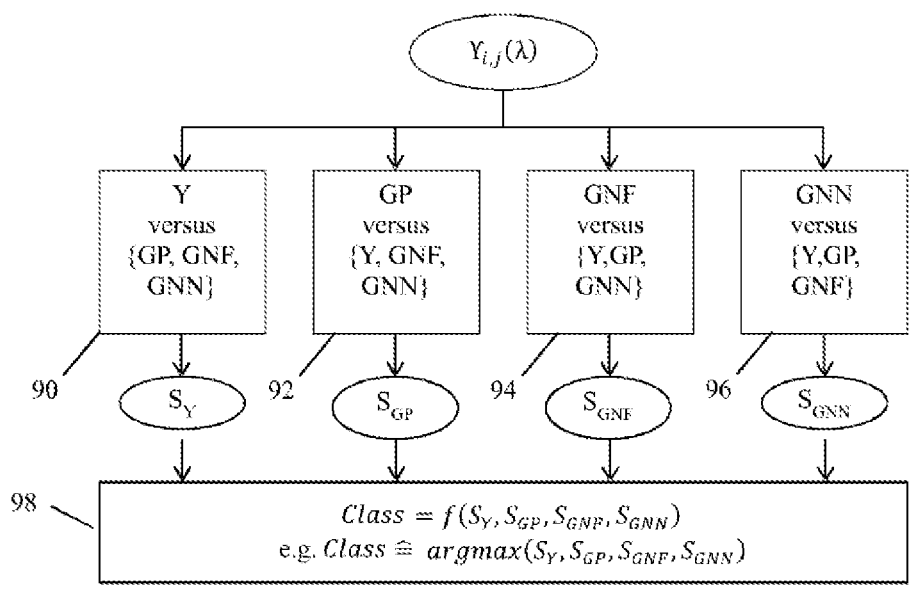
FIG. 7A is a graph illustrating a flat prediction model of the classes Y, GP, GNF, GNN.

The first type of prediction model, shown in FIG. 7A, consists of learning four "one against all" prediction models 90, 72, 74, 76, namely a prediction of the class Y against the classes GP, GNF, GNN, a prediction of the class GP against the classes Y, GNF, GNN, a prediction of the class GNF against the classes Y, GP, GNN and a prediction of the class GNN against the classes Y, GP, GNF. For this purpose:

each prediction model is learned from the learning database by implementing one of the learning tools described above in relation to the relationships (6) or (7), the class Cl being equal to Y, GP, GNF GNN and the set $\overline{Cl}$ being made up of the other three classes;

The prediction of the Gram type and the fermentative character of a pixel (step 52 in FIG. 3) is obtained by calculating (steps 90-96), the distances $S_Y$, $S_{GP}$, $S_{GNF}$, $S_{GNN}$ of the spectrum $Y_{i,j}(\lambda)$ of said pixel respectively to the hyperplanes $(\widehat{\beta_R^Y}, \beta_0^Y)$ $(\widehat{\beta_R^{GP}}, \beta_0^{GP})$, $(\widehat{\beta_R^{GNF}}, \beta_0^{GNF})$, $(\widehat{\beta_R^{GNN}}, \beta_0^{GNN})$, or to the hyperplanes hyperplanes $(\widehat{\beta^Y}, \beta_0^Y)$, $(\widehat{\beta^{GP}}, \beta_0^{GP})$, $(\widehat{\beta^{GNF}}, \beta_0^{GNF})$, $(\widehat{\beta^{GNN}}, \beta_0^{GNN})$, and then determining the class of the pixel, in 88, as a function of the calculated distances. In particular, the class selected is the one corresponding to the maximum distance.

According to the first type of structure shown in FIG. 7A, called "flat", the classes Y, GP, GNF and GNN are considered to be of equal importance, and therefore the identification errors as well. For example, identifying a yeast Y instead of a bacterium GNN is as serious as identifying a bacterium GNF instead of a bacterium GNN. According to the structure illustrated in FIG. 7B, the prediction models are organized according to a phylogenetic taxonomic tree, which makes it possible to no longer consider the different classes with equal importance and to introduce a priori information, i.e. evolutionary information that can influence the shape of the spectra. More specifically, this prediction model tree includes:

a first model 100 consisting in distinguishing yeasts Y from bacteria GP, GNF, GNF;

a second model 102 to distinguish bacteria GP from bacteria GNF and GNN; and a third model 104 consisting of distinguishing bacteria GNF from bacteria GNN.

Each of the models 100-104 is obtained in the manner described above in relation to the relationships (6) or (7) and the prediction of the membership of a pixel spectrum $Y_{i,j}(\lambda)$ to one of the classes Y, GP, GNF and GNN thus consists in calculating its distance $S_Y$ to the hyperplane of the first model 100 and if the sign of this distance is positive, the class Y is then predicted. Otherwise, the distance $S_{GP}$ to the hyperplane of the second model 102 is calculated and if the sign of this distance is positive, then the class GP is predicted. Otherwise, the distance $S_{GNF}$ to the hyperplane of the third model 104 is computed, then the class GNF is predicted. Otherwise the class GNN is predicted.

Figure 7B:
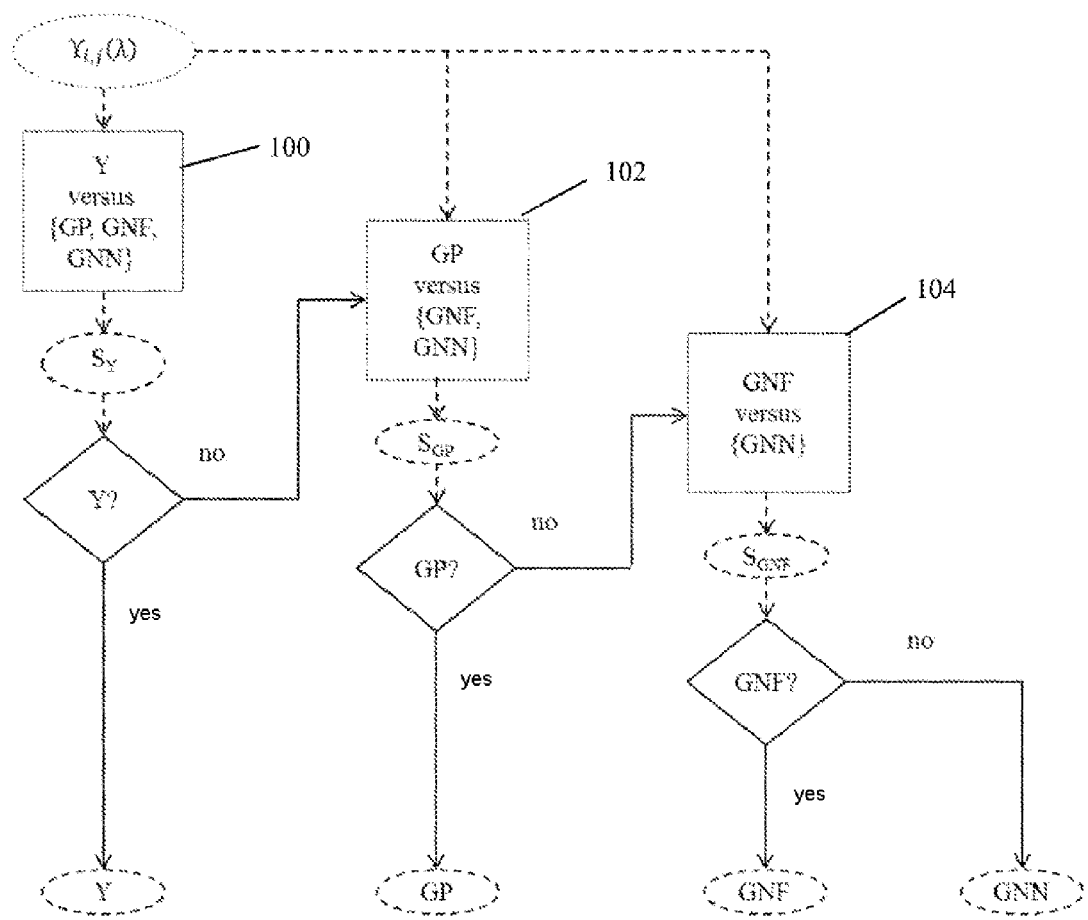
FIG. 7B is a graph illustrating a hierarchical prediction model based on a phylogenetic tree of classes Y, GP, GNF, GNN.
Figure 7C:
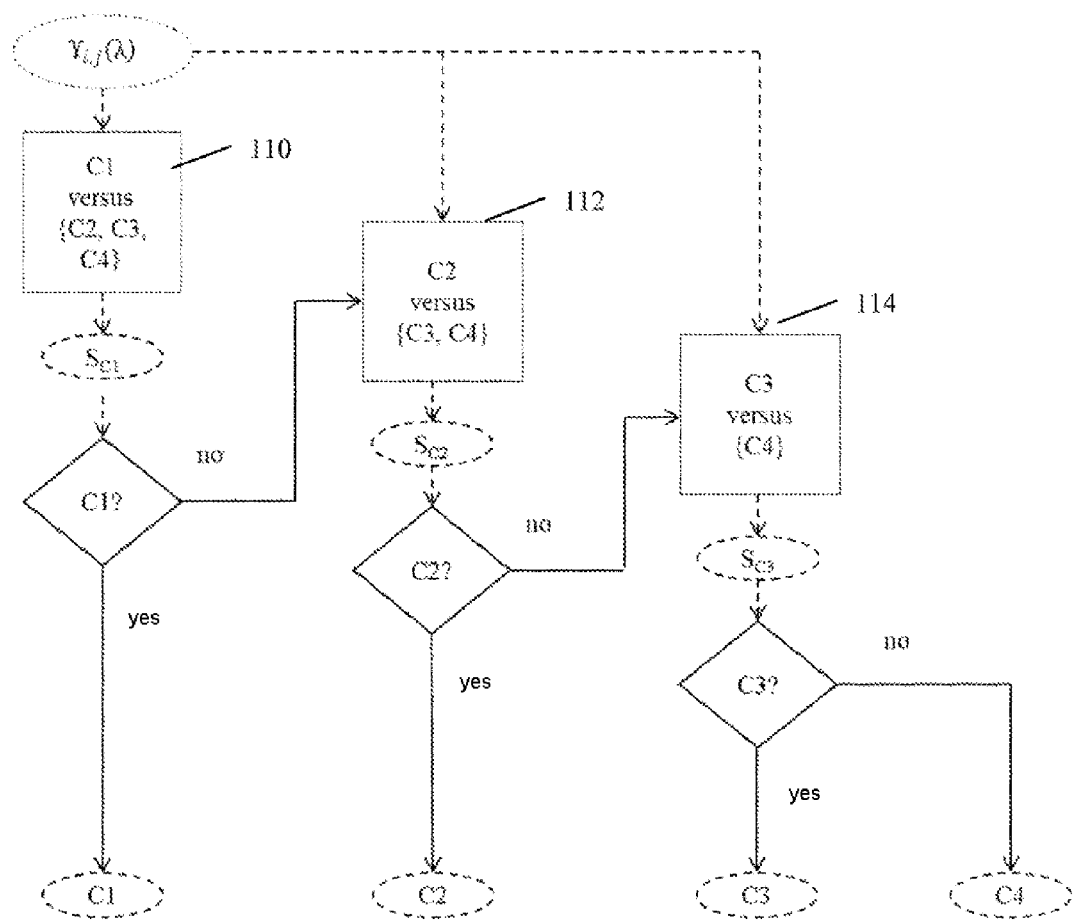
FIG. 7C is a graph illustrating a hierarchical prediction model based on an optimal tree of classes Y, GP, GNF, GNN.

While the phenotypic model improves the accuracy of prediction compared to a flat prediction structure as shown in FIG. 7A, the inventors noted that the phenotypic tree is not necessarily the tree that gives better results. In particular, a tree may be preferred depending on the culture medium on which the microorganisms to be characterized have grown, which influences the shape of the spectra. Preferably, an optimal prediction structure, as shown in FIG. 7C, is determined as a function of the calibration spectra. In particular, in a first step, the four prediction models a) Y versus GP, GNF and GNN, b) GP versus Y, GNF and GNN, c) GNF versus Y, GP and GNN, and d) GNN versus Y, GP and GNF are calculated as described above and the model with the best prediction performance is retained to be the first model 110 of the optimal tree. In a second step, the class of the first model is discarded, and the three prediction models corresponding to the remaining classes are computed. For example, if the first model corresponds to the class GNN, then the three models of the second step are a) Y versus GP and GNF, b) GP versus Y, and GNF, and c) GNF versus Y and GP as described above. The best of the three models is then retained to be the second model 112 of the optimal tree. In a third step, the classes of the first and second models 110 and 112 are discarded, and a prediction model between the two remaining classes is computed as described above and kept as the third model 114 of the optimal tree. The prediction of the membership of a pixel spectrum $Y_{i,j}(\lambda)$ to one of the classes Y, GP, GNF and GNN is then obtained by traversing the tree in a manner similar to that described in relation to FIG. 7B.

Returning to FIG. 6, once the structure of the prediction model has been determined, the learning process 80 continues, optionally in 84, with a reduction in the number of spectral channels used for prediction, this reduction being achieved by channel selection and/or grouping. In particular, when the prediction models previously described in relation to FIGS. 7A, 7B and 7C, are calculated using the "step-forward" approach of FIG. 5, the number of channels used can be fixed directly by the parameter R. Alternatively, or additionally, additional channels that do not provide any significant increase in model performance can be discarded. Alternatively or additionally, channel grouping can be achieved by dividing the range 390 nm-900 nm into intervals whose width corresponds to the width of the filters as described above in connection with FIGS. 2 and 3. Only one spectral channel is then retained per interval. A final number of channels where $\lambda_1, \lambda_2, \ldots, \lambda_{N_F}$ are thus selected and define the center wavelengths of the spectral filters of set 36 of the multispectral system in FIG. 2. As will be described below, it is possible to obtain a prediction of the high-precision classes using only 24 channels, and thus 24 spectral filters.

Optionally, having selected the final channels for the multispectral application and constructed the multispectral system accordingly, a new training, based on the acquisition of spectra with the system of FIG. 2, is implemented to refine the prediction models, this training being analogous to that described in relation to FIGS. 6 and 7.

Similarly, the selection of a predetermined number R of discriminating channels has been described. Alternatively, this number is not fixed a priori and a stopping criterion for the slot search is a stagnation of the performance gain as a function of the number of channels. If, for example, the addition of at least one channel does not increase the performance, for example the BCR detailed below, by more than X %, then the channel search is stopped, with for example X less than or equal to 2%.

C. EXAMPLES

An application of the predictions of classes Y, GP, GNF and GNN will now be described. For this purpose, 21 bacterial and yeast strains are used, these microbial species being described in FIG. 8. These species were cultured for 24 hours on COS agar and TSA agar, resulting in a learning database for each of these media. The colony and pixel counts for each species and medium are shown in FIG. 9 (COS) and FIG. 10 (TSA), respectively, with Block 1 corresponding to calibration data and Block 2 corresponding to cross-validation data.

The performance of class prediction is advantageously calculated as the average of the sensitivities of the class predictions (rate of well-ranked spectra). This weighted criterion, also called "balance classification rate" or "BCR", makes it possible to take into account pixel counts that are unbalanced, which is the case due to the size of the colonies, which is variable depending on the species. The calculation of the BCR is shown in FIG. 11.

C.1. COS Results

C.1.1. Flat Model

Table 1 below gives the BCRs for a flat prediction model shown in FIG. 7A and for prediction models obtained using the relationships (7).

TABLE 1

|  | Calibration | Cross-validation |
| --- | --- | --- |
| Y versus GP + GNN + G NF | 85% | 84% |
| GP versus Y + GNN + GNF | 93% | 91% |
| GNN versus Y + GP + GNF | 80% | 80% |
| GNF versus Y + GP + GNN | 99% | 99% |

It is immediately apparent from Table 1 that it is possible to accurately predict the different strains of bacteria. In particular, knowing that the microorganism to be characterized is a bacterium, it is possible to predict its Gram type and its fermentative or non-fermentative character, by implementing a first prediction GP versus GNN and GNF and a second prediction GNN versus GP and GNF. This type of prediction is particularly useful for the selection of consumables for the performance of an antibiogram with the Vitek®2 platform marketed by the applicant.

C.1.2. Optimal Tree

The BCRs for the models 110, 112, 114 shown in FIG. 7C and obtained using the relationships (7) are summarized in Table 2.

TABLE 2

|  | Calibration | Cross-validation |
|---|---|---|
| 110: GNF versus Y + GP + GNN | 99% | 99% |
| 112: GP versus Y + GNF | 91% | 90% |
| 114: Y versus GNF | 86% | 84% |

It is noted that the optimal tree differs significantly from the phylogenetic tree, with the influence of the COS medium likely to be greater than the influence of phylogenetic differences.

The BCRs for the models 110, 112, 114 shown in FIG. 7C and obtained using the step-forward approach in FIG. 4 and the relationships (6), with R=24 for each model, are summarized in Table 3 (See FIG. 21).

Note from Table 3 that the performance gain is limited from the $8^{th}$ channel for the first model, and from the $4^{th}$ channel for the third model. To obtain a multispectral application using 24 spectral filters, corresponding to the filter systems on the market, it is therefore advantageous to select 8 channels, 14 channels and 4 channels respectively for the first, second and third models 110, 112, 114. The performance of this embodiment is summarized in Table 4.

TABLE 4

|  | Most discriminating channel selection order | Wavelength (nm) | BCR |
|---|---|---|---|
| GNF versus Y + GP + GNN | 1 | 613.58 | 97.10% |
|  | 2 | 484.16 |  |
|  | 3 | 634.45 |  |
|  | 4 | 605.23 |  |
|  | 5 | 588.53 |  |
|  | 6 | 640.71 |  |
|  | 7 | 607.31 |  |
|  | 8 | 434.06 |  |
| GP versus Y + GNF | 1 | 634.45 | 93.30% |
|  | 2 | 598.97 |  |
|  | 3 | 665.76 |  |
|  | 4 | 630.28 |  |
|  | 5 | 864.07 |  |
|  | 6 | 548.87 |  |
|  | 7 | 488.33 |  |
|  | 8 | 628.19 |  |
|  | 9 | 661.59 |  |
|  | 10 | 584.35 |  |
|  | 11 | 530.08 |  |
|  | 12 | 636.54 |  |
|  | 13 | 603.14 |  |
|  | 14 | 486.25 |  |
| Y versus GNF | 1 | 613.58 | 95.90% |
|  | 2 | 651.15 |  |
|  | 3 | 425.71 |  |
|  | 4 | 617.75 |  |

Of course other numbers of channels can be selected depending on the number of spectral filters available for the system in FIG. 2.

Figure 12:
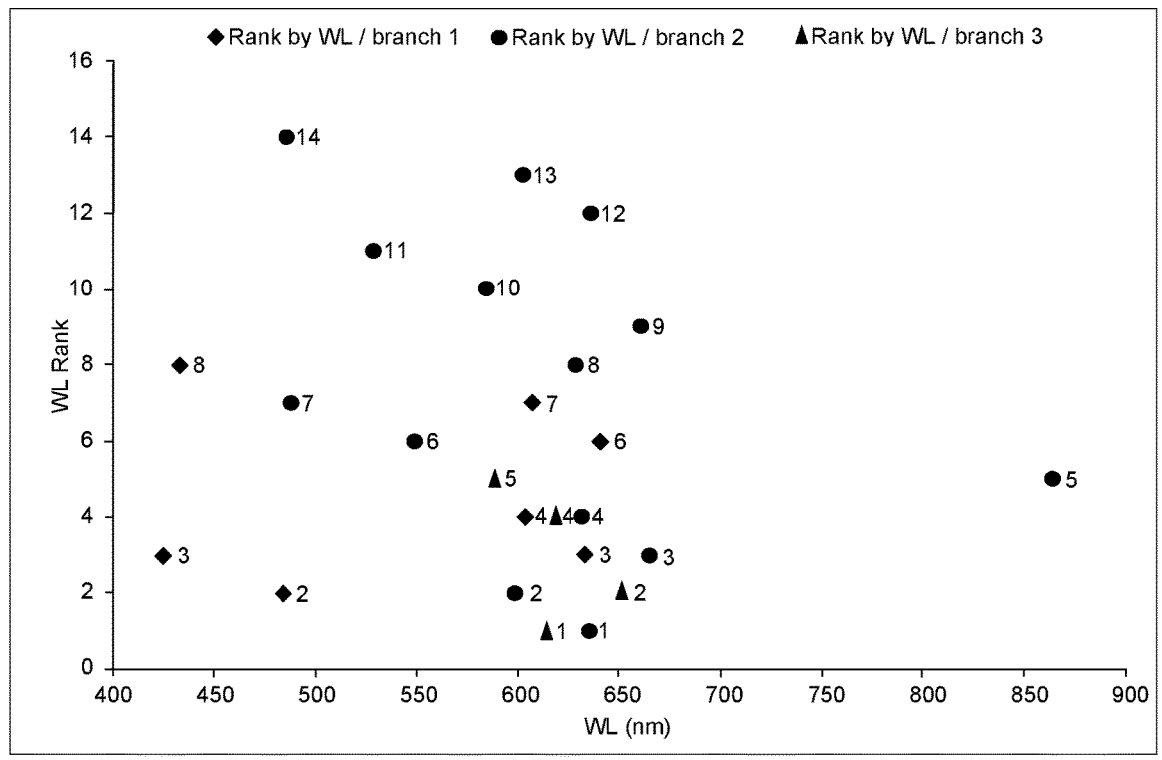
FIG. 12 is a graph illustrating the spatial distribution of the main discriminant spectral channels for the optimal tree of the COS medium.
Figure 13:
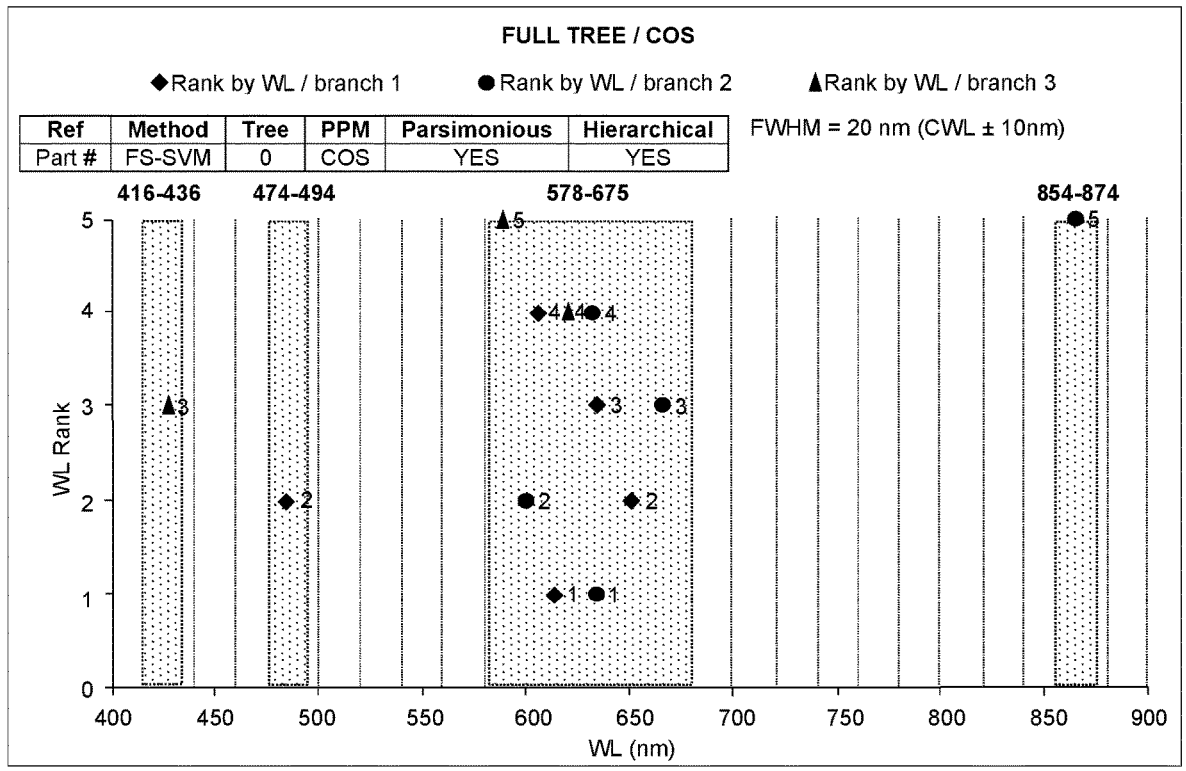
FIG. 13 is a graph illustrating the spatial distribution of the 5 main discriminant spectral channels of each model for the optimal tree of the COS medium.
Figure 14:
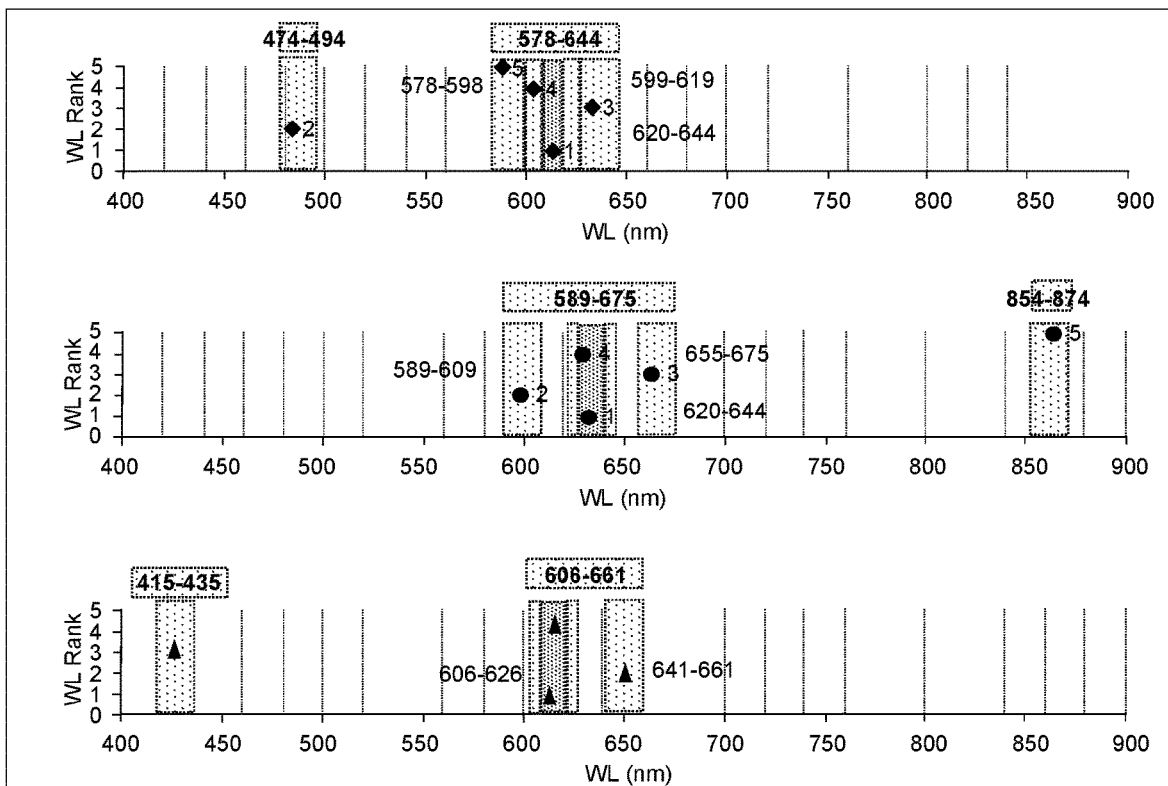
FIG. 14 is a graph showing individually the five main discriminant channels of each model of the optimal tree of the COS environment.

Also note that the "step-forward" approach makes it possible to determine the spectral ranges containing the information necessary for class prediction. By limiting itself to the first five channels of each model, BCRs close to or greater than 90% are obtained respectively. The spectral distribution of these channels is shown in FIGS. 12 to 14. This clearly distinguishes distinct spectral bands more than 50 nm apart. In particular:

A. The four classes Y, GP, GNF and GNN can be predicted efficiently using only spectral information in a first range 415-500 nm and a second range 535-675 nm. Using these ranges only, BCRs are greater than or equal to 90%. By limiting the first range to 575-675 nm, 4 channels are used only per model for BCR close to or greater than 90%. Optionally a third range 850-875 nm, corresponding to the channel rank 5 of the second model is used. In particular, prediction in the first range 415-500 nm can be performed only in the ranges 415-440 nm and 470-495 nm. The invention thus covers any prediction process for the classes Y, GP, GNF and GNN consisting of acquiring spectra in said ranges and predicting the classes as a function of said spectra only in said ranges. It is further noted that if the invention makes it possible to distinguish between the classes Y, GP, GNF and GNN, it thus makes it possible to distinguish between yeasts and bacteria, using the spectral information contained in the aforementioned ranges. The invention therefore also covers a process for predicting the yeast or bacterial character of a microorganism to be characterized;

B. the prediction of the class GNF against Y+GP+GNN can be efficiently performed only on a first range 470-500 nm and a second range 575-645 nm. The invention thus covers any process for predicting the class GNF consisting of acquiring spectra in said ranges and predicting the class GNF as a function of said spectra only in said ranges. It should be noted that when the bacterial character of the microorganism to be characterized is already known, the prediction then consists of predicting the class GNF against GP and GNN. The invention therefore also covers this type of prediction based solely on the 470-500 nm and 575-645 nm ranges;

C. class GP versus Y+GNN prediction can be effectively performed only in the first range 535-675 nm, and more specifically in the range 585-675 nm, and the second range 850-875 nm. The invention thus covers any process for predicting the class GP consisting of acquiring spectra in said ranges and predicting the class GP as a function of said spectra only in said ranges. It should be noted that when the bacterial character of the microorganism to be characterized is already known, the prediction then consists in predicting the class GP against the classes GNF and GNN, and consequently by the class GP against the class of Gram-negative (GN) bacteria. The invention therefore also covers this type of prediction based solely on the 535-675 nm range, and more particularly on the 585-675 nm range, and the 850-875 nm range;

D. By combining the predictions described in points B and C below, note that with three ranges, and knowing the bacterial character of the microorganism to be characterized, it is possible to determine whether a bacterial colony is GP, GNF or GNN. This type of prediction is particularly useful for the selection of consumables for carrying out an antibiogram with the Vitek®2 platform marketed by the applicant.

C.1.3. Phylogenetic Tree

The BCRs for the models 100, 102, 104 shown in FIG. 7B and obtained using the relationships (7) are summarized in Table 5.

TABLE 5

|  | Calibration | Cross-validation |
|---|---|---|
| 100: Y versus GP + GNN + GNF | 85% | 84% |
| 102: GP versus GNN + GNF | 95% | 96% |
| 104: GNF versus GNN | 97% | 97% |

C.2. TSA Results
C.2.1. Flat Model

Table 1 below gives the BCRs for a flat prediction model shown in FIG. 7A and for prediction models obtained using the relationships (7).

TABLE 6

|  | Calibration | Cross-validation |
|---|---|---|
| Y versus GP + GNN + GNF | 89% | 88% |
| GP versus Y + GNN + GNF | 91% | 90% |
| GNN versus Y + GP + GNF | 75% | 73% |
| GNF versus Y + GP + GNN | 90% | 88% |

C.2.2. Optimal Tree

The BCRs for the models 110, 112, 114 shown in FIG. 7C and obtained using the relationships (7) are summarized in Table 7.

TABLE 7

|  | Calibration | Cross-validation |
|---|---|---|
| 110: GP versus Y + GNF + GNN | 91% | 90% |
| 112: Y versus GNF + GNN | 94% | 93% |
| 114: GNF versus GNN | 82% | 81% |

Note that the optimal tree differs significantly from the phylogenetic tree, with the influence of the COS medium likely to be greater than the influence of phylogenetic differences.

The BCRs for the models 110, 112, 114 shown in FIG. 7C and obtained using the step-forward approach in FIG. 5 and the relationships (6), with R=24 for each model, are summarized in Table 8 (see FIG. 22).

Figure 15:
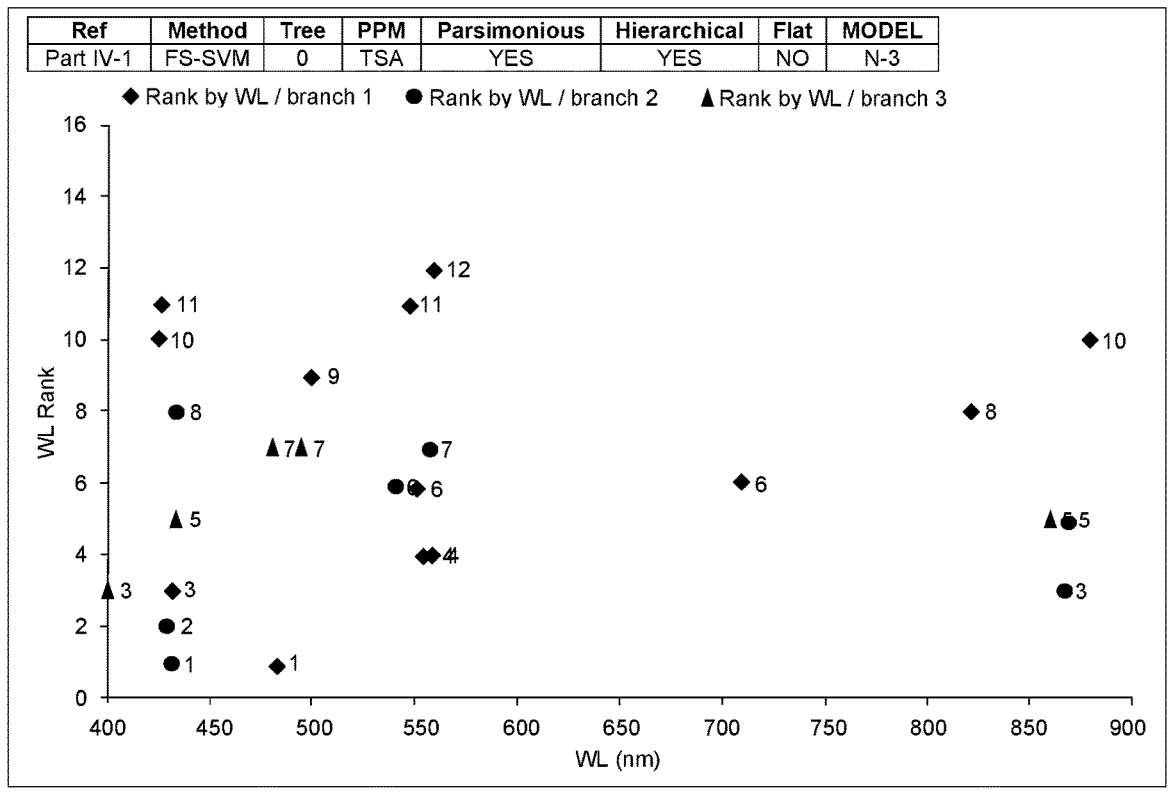
FIG. 15 is a graph illustrating the spatial distribution of the main discriminant spectral channels for the optimal tree of the TSA medium.
Figure 16:
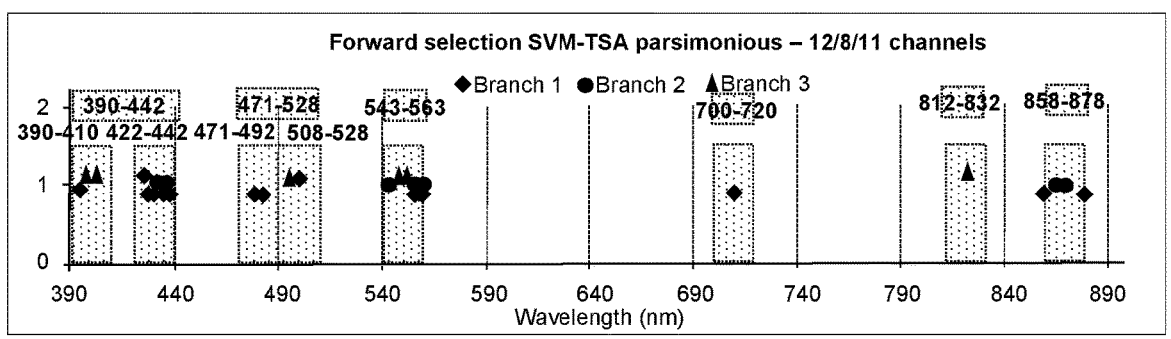
FIG. 16 is a graph illustrating the spatial distribution of the main discriminant spectral channels for the optimal tree of the COS medium.
Figure 17:
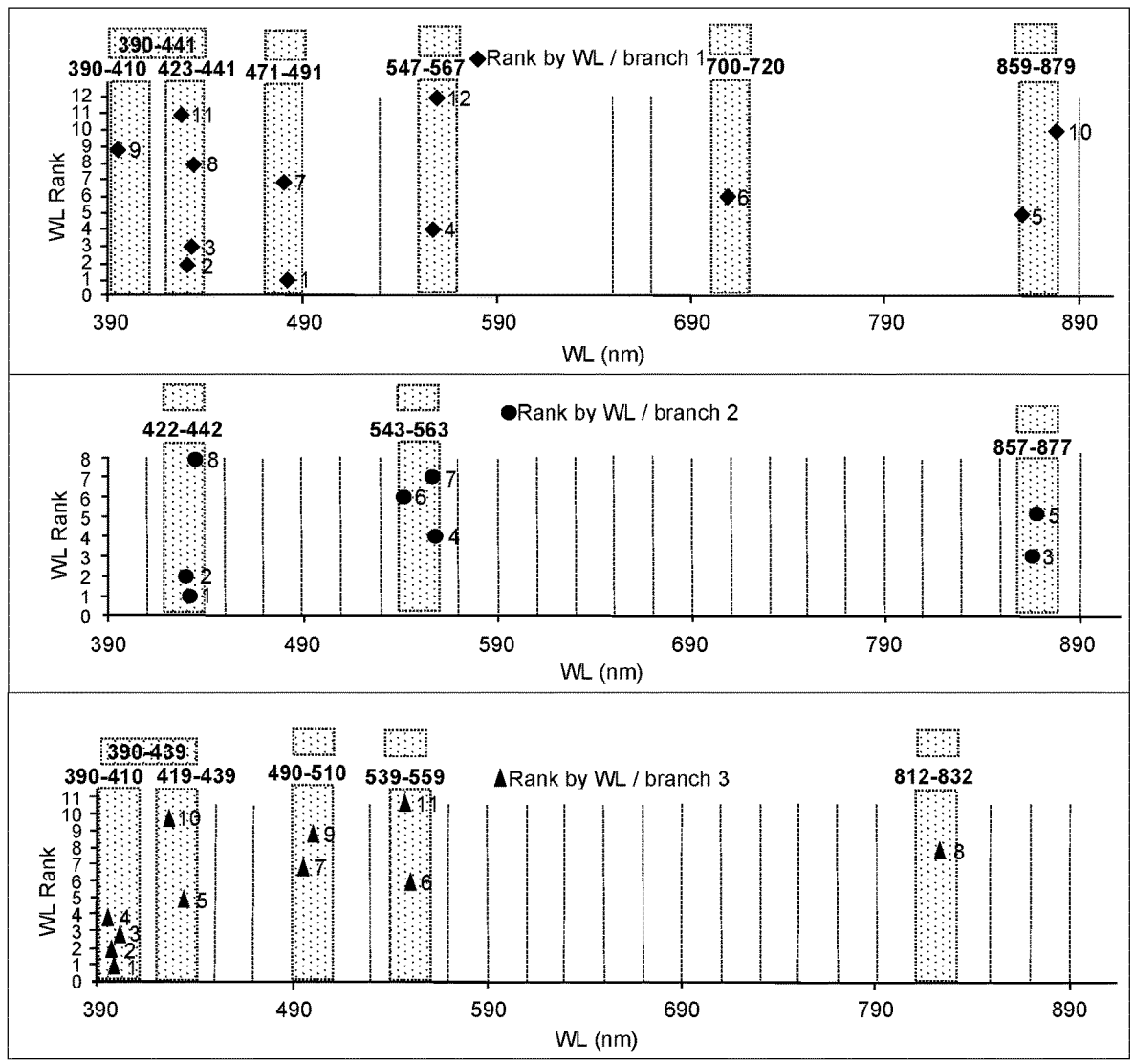
FIG. 17 is a graph illustrating the 12, 8, and 11 main discriminant channels associated with the first, second, and third prediction models of the optimal tree of the TSA medium, respectively.

FIGS. 15 to 17 illustrate the spectral distribution of the main branch channels, in the same graph (FIG. 15), in a parsimonious approach with 12, 8 and 11 channels for the first, second and third models 110, 112 and 114, (FIG. 16) and by model (FIG. 17).

C.2.3. Phylogenetic Tree

The BCRs for the models 100, 102, 104 shown in FIG. 7B and obtained using the relationships (7) are summarized in Table 9.

TABLE 9

|  | Calibration | Cross-validation |
|---|---|---|
| 100: Y versus GP + GNN + GNF | 89% | 88% |
| 102: GP versus GNN + GNF | 92% | 92% |
| 104: GNF versus GNN | 82% | 81% |

The BCRs for the models 100, 102, 104 shown in FIG. 7B and obtained using the step-forward approach in FIG. 4 and the relationships (6), with R=24 for each model, are summarized in Table 10 (see FIG. 23).

Figure 18:
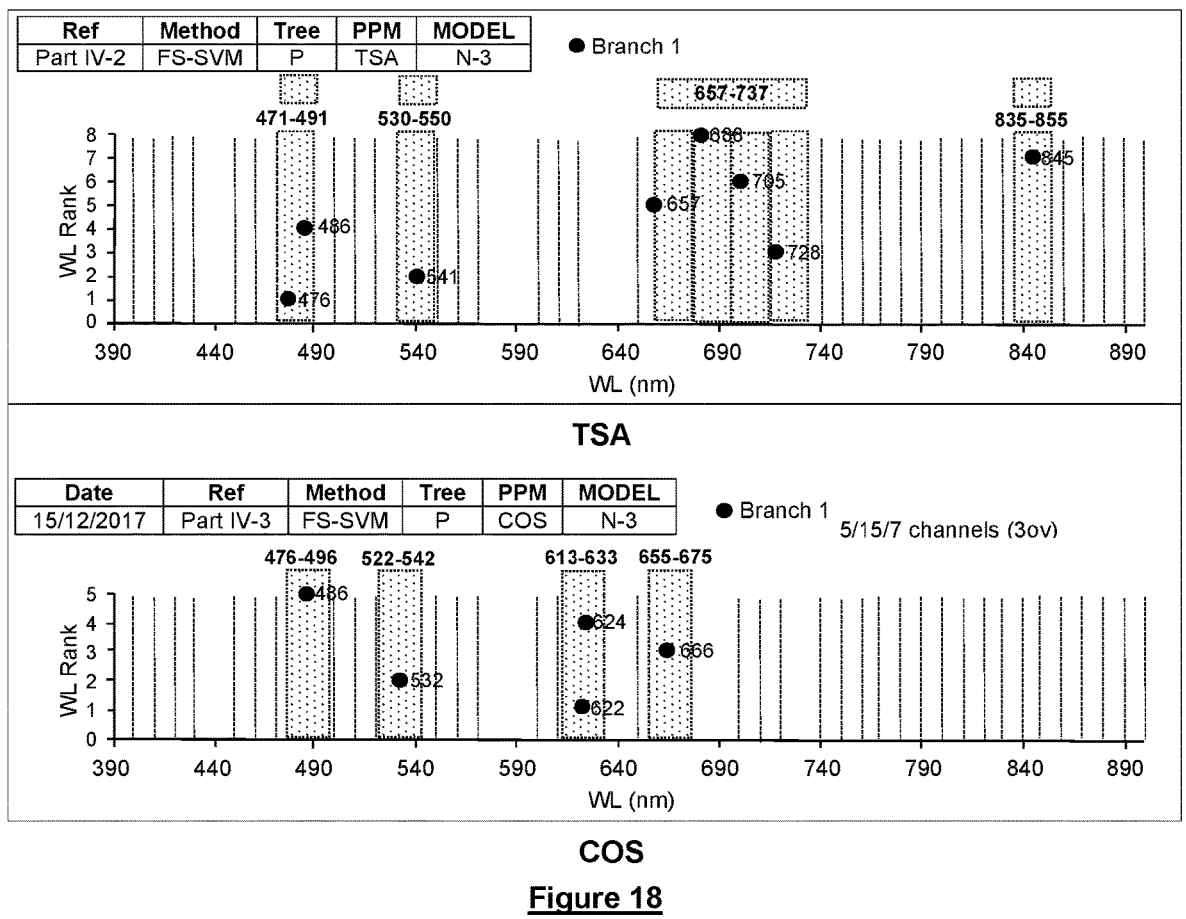
FIGS. 18 to 20 are graphs showing the first, second and third prediction models of the phylogenetic tree, respectively, with the graph at the top of each figure corresponding to the TSA medium and the graph at the bottom of each figure corresponding to the COS medium.
Figure 19:
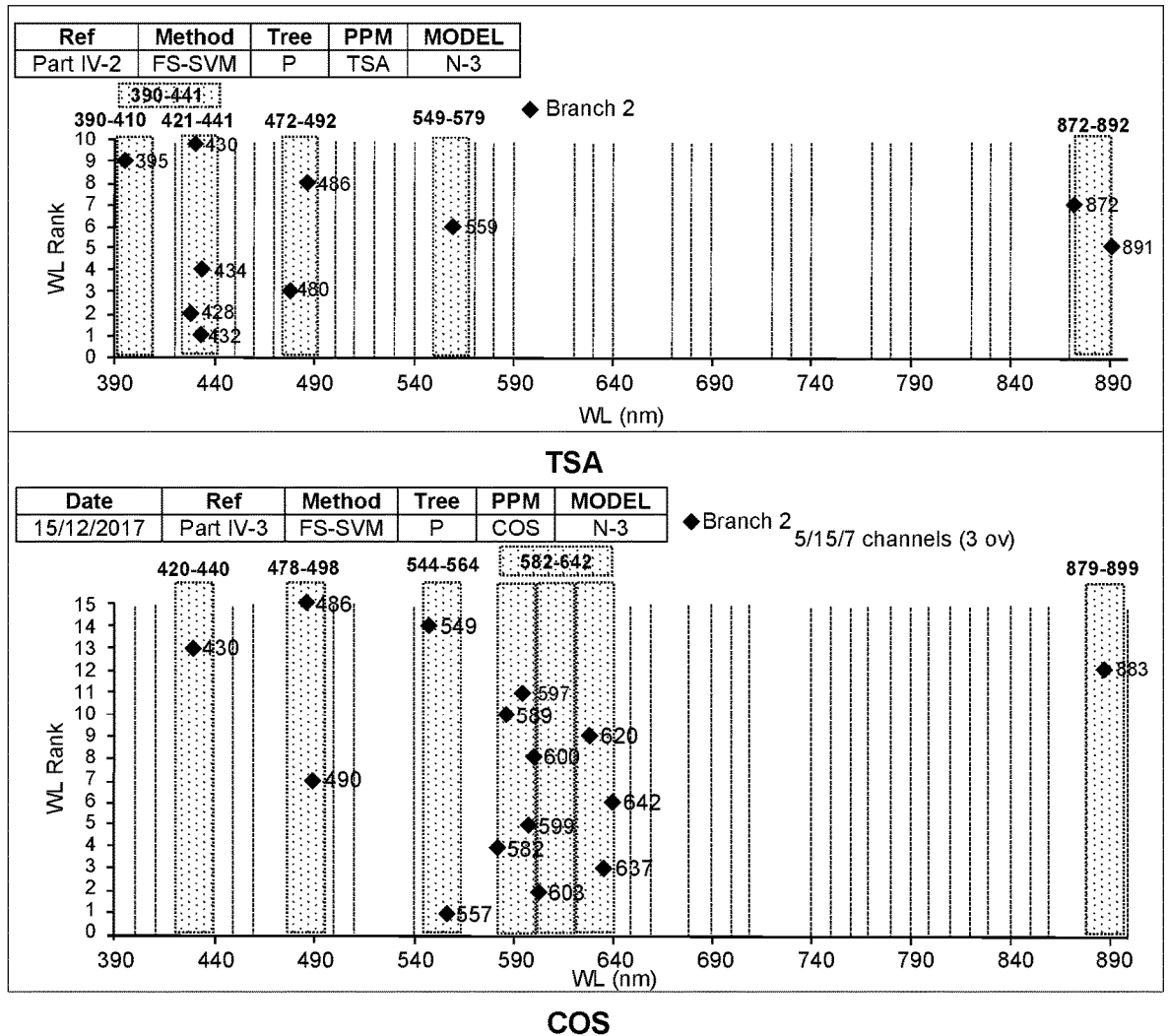
Figure 20:
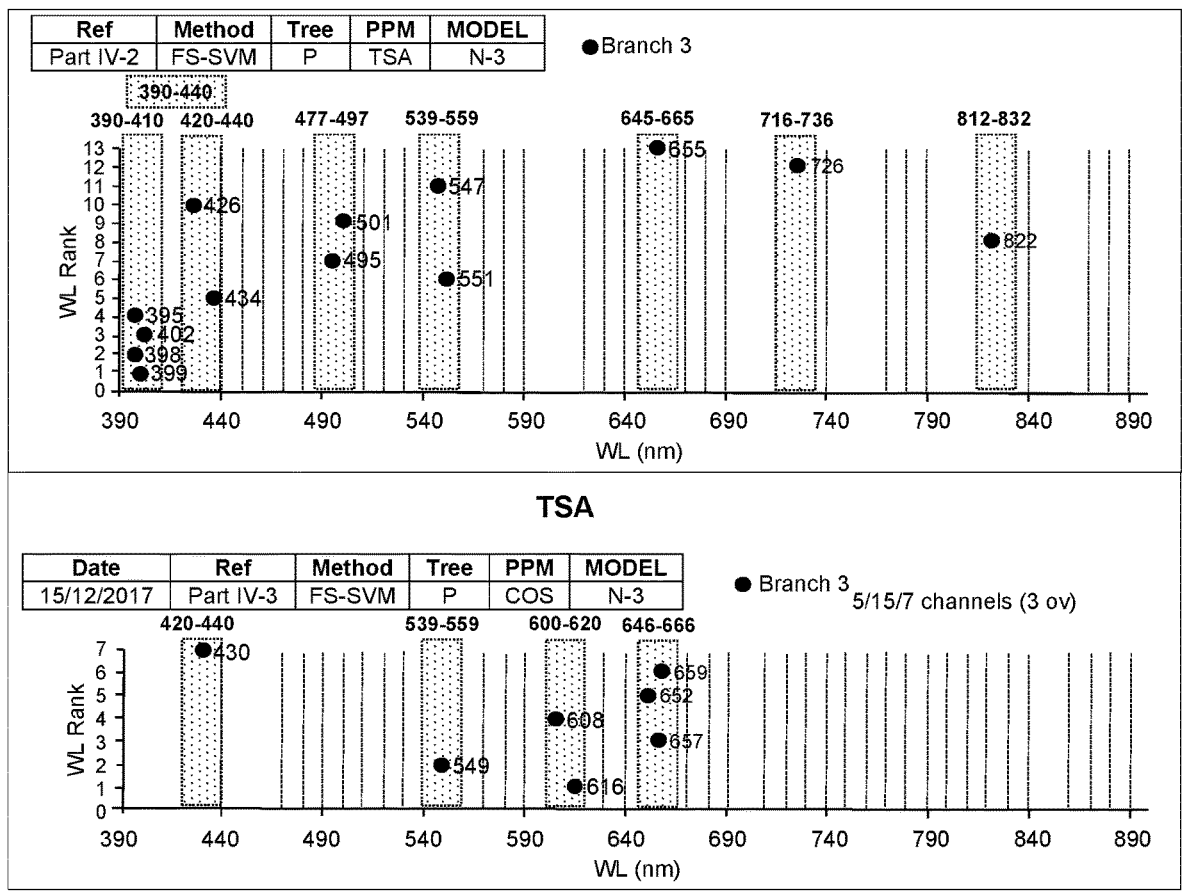

FIGS. 18 to 20 show the spectral distribution of the main spectral channels, model by model, with the TSA medium at the top of each of these figures and in comparison with the COS medium at the bottom of each of the figures.

The invention claimed is:

1. A process for detecting the Gram type and the fermentative character of a bacterial strain, comprising:
    illuminating in a wavelength range 390 nm-900 nm at least one bacterium of the strain having a natural electromagnetic response in the range, wherein the illuminating covers one or more wavelength ranges, wherein the one or more wavelength ranges cover at least two distinct spectral bands whose center wavelengths are more than 50 nm apart;
    acquiring, within the range, a luminous intensity reflected from or transmitted through the illuminated bacterium; and
    determining the Gram type and the fermentative character of the bacterial strain as a function of the luminous intensity acquired in the range, by applying an automated prediction model,
    wherein the prediction model includes at least ne class identifying the Gram type of the bacterial strain,
    wherein the prediction model includes at least ne class identifying the fermentative character of the bacterial strain,
    wherein the prediction model does not include a class identifying the microorganism at a species level.

2. The detection process as claimed in claim 1, wherein the determination of Gram type and fermentative character comprises applying a first classification of the prediction model predicting whether the acquired luminous intensity is the luminous intensity of a fermentative Gram-negative bacterial strain.

3. The detection process as claimed in claim 1, wherein the determination of the Gram type and the fermentative character comprises applying at least one selected from the group of: a classification of the prediction model predicting whether the acquired luminous intensity is the luminous intensity of a Gram-positive bacterial strain, and a classification of the prediction model predicting whether the acquired luminous intensity is the luminous intensity of a Gram-negative bacterial strain.

4. The detection process as claimed in claim 1, wherein the determination of the Gram type and the fermentative character further comprises applying a classification of the prediction model predicting whether the acquired luminous intensity is the luminous intensity of a yeast or a microbiological test distinguishing the bacterial strain from a yeast.

5. The detection process as claimed in claim 2, wherein:
    the illumination and acquisition are performed directly on a sample comprising a colony of the bacterial strain and a nutrient medium on which the colony has grown, the nutrient medium being a blood agar;
    if the acquired luminous intensity is not the luminous intensity of a fermentative Gram-negative bacterial strain, the determination of the Gram type and fermentative character further comprises applying a second classification of the prediction model predicting whether the acquired luminous intensity is the luminous intensity of a Gram-positive bacterial strain.

6. The detection process as claimed in claim 5, wherein, if the acquired luminous intensity is not the luminous intensity of a Gram-positive bacterial strain, the determination of the Gram type and of the fermentative character further comprises applying a third classification of the prediction model predicting whether the acquired luminous intensity is the luminous intensity of a yeast.

7. The process as claimed in claim 6, wherein
    the first classification predicting whether the acquired luminous intensity is the luminous intensity of a Gram-negative and fermentative bacterial strain is a classification distinguishing the luminous intensity of Gram-negative and fermentative bacterial strains from the luminous intensity of the group consisting of Gram-negative and non-fermentative bacterial strains, Gram-positive bacterial strains, and yeasts;
    the second classification predicting whether the acquired luminous intensity is the luminous intensity of a Grampositive bacterial strain is a classification distinguishing the luminous intensity of Gram-positive bacterial strains from the luminous intensity of the group consisting of negative and non-fermentative bacterial strains, and yeasts;

the third classification predicting whether the acquired luminous intensity is the luminous intensity of a yeast is a classification distinguishing the luminous intensity of yeasts from the luminous intensity of the group consisting of Gram-negative and non-fermentative bacterial strains.

8. The process as claimed in claim 4, wherein, if the acquired luminous intensity is not the luminous intensity of a yeast, the determination of the Gram type and of the fermentative character further comprises applying a classification of the prediction model predicting whether the acquired luminous intensity is the luminous intensity of a Gram-positive bacterial strain.

9. The process as claimed in claim 8, wherein, if the acquired luminous intensity is not the luminous intensity of a Gram-positive bacterial strain, the determination of the Gram type and of the fermentative character further comprises applying a classification of the prediction model predicting whether the luminous intensity is the luminous intensity of a fermentative Gram-negative bacterial strain or of a non-fermentative Gram-negative bacterial strain.

10. The process as claimed in claim 9, wherein:
the classification predicting whether the acquired luminous intensity is the luminous intensity of a yeast is a classification of the prediction model distinguishing the luminous intensity of yeasts from the luminous intensity of the group consisting of Gram-positive bacterial strains, Gram-negative and non-fermentative bacterial strains, and Gram-negative and fermentative bacterial strains;
the classification predicting whether the luminous intensity is the luminous intensity of a Gram-positive bacterial strain is a classification of the prediction model distinguishing the luminous intensity of Gram-positive bacterial strains from the luminous intensity of the combination of Gram-negative and non-fermentative bacterial strains and Gram-negative and fermentative bacterial strains;
the classification predicting whether the luminous intensity is the luminous intensity of a fermentative Gram-negative bacterial strain or a non-fermentative Gram-negative bacterial strain is a classification of the prediction model distinguishing the luminous intensity of Gram-negative non-fermentative bacterial strains from the luminous intensity of the group consisting of Gram-negative and fermentative bacterial strains.

11. The process as claimed in claim 3, wherein:
the illumination and acquisition are performed directly on a sample comprising a colony of the bacterial strain and a nutrient medium on which the colony has grown, the nutrient medium being Tryptone-Soy agar;
if the acquired luminous intensity is not that of a Gram-positive bacterial strain, the determination of the Gram type and the fermentative character further comprises applying a classification of the prediction model predicting whether the acquired luminous intensity is the luminous intensity of a yeast.

12. The process as claimed in claim 11, wherein, if the acquired luminous intensity is not the luminous intensity of a yeast, the determination of the Gram type and of the fermentative character further comprises applying a classification of the prediction model predicting whether the luminous intensity is the luminous intensity of a fermentative Gram-negative bacterial strain or of a non-fermentative Gram-negative bacterial strain.

13. The process as claimed in claim 12, wherein:
the classification predicting whether the luminous intensity is the luminous intensity of a Gram-positive bacterial strain is a classification distinguishing the luminous intensity of Gram-positive bacterial strains from the luminous intensity of the group consisting of Gram-negative and non-fermentative bacterial strains, Gram-negative and fermentative bacterial strains, and yeasts;
the classification predicting whether the acquired luminous intensity is the luminous intensity of the yeast is a classification distinguishing the luminous intensity of the yeast from the luminous intensity of the group consisting of negative and non-fermentative bacterial strains and negative and fermentative bacterial strains;
the classification predicting whether the luminous intensity is the luminous intensity of a fermentative Gram-negative bacterial strain or a non-fermentative Gram-negative bacterial strain is a classification distinguishing the luminous intensity of Gram-negative non-fermentative bacterial strains from the luminous intensity of the group consisting of Gram-negative and fermentative bacterial strains.

14. The process as claimed in claim 2, wherein each of the classifications is learned from hyperspectral images in the range 390 nm-900 nm and according to an approach comprising stepwise increasing a set of spectral channels used in the classification until a predetermined accuracy threshold or a predetermined maximum number of channels is reached.

15. The detection process as claimed in claim 2, wherein the first classification distinguishes between luminous intensities in the wavelength range 470 nm-500 nm and the wavelength range 575-645 nm only.

16. The detection process as claimed in claim 3, wherein the applied classification distinguishes between luminous intensities as a function of the wavelength range 535 nm-675 nm and the wavelength range 850 nm-875 nm only.

17. The detection process as claimed in claim 5, wherein the second classification distinguishes luminous intensities according to the wavelength range 415 nm-500 nm and the wavelength range 535 nm-675 nm only.

18. The detection process as claimed in claim 1, wherein the luminous intensity is acquired on a number of spectral channels less than or equal to 24.

19. The detection process as claimed in claim 5, wherein the luminous intensity is acquired on a number of spectral channels less than or equal to 5 for each of the first and second classifications.

20. The detection process as claimed in claim 1, wherein the acquisition of the luminous intensity comprises the acquisition of a hyperspectral or multispectral image of a colony of bacteria of the strain, and wherein the luminous intensity is determined as a function of at least one pixel of the image corresponding to the colony.

21. The detection process as claimed in claim 20, wherein a respective first prediction of the Gram type and the fermentative character is carried out as a function of the light intensity of each pixel of a set of pixels of the colony, and wherein the Gram type and the fermentative character are determined by a majority vote of results of the first predictions.

22. The detection process as claimed in claim 21, wherein the majority vote is a 70% or more pixel vote.

23. A process for producing an antibiogram of a bacterial strain to an antibiotic comprising:
  determining the Gram type and the fermentative character of the bacterial strain according to the process as claimed in claim 1;
  providing at least one sample comprising the bacterial strain, a culture medium and a concentration of an antibiotic as a function of the Gram type and the selected fermentative character; and
  determining the sensitivity of the bacterial strain to the antibiotic as a function of the growth of the strain in the sample.

24. A process for identifying a bacterial strain to an antibiotic comprising:
  determining the Gram type and the fermentative character of the bacterial strain according to the process as claimed in claim 1;
  selecting at least one colorimetric medium according to the Gram type and the selected fermentative character; and
  culturing the bacterial strain in the medium.

25. A system for detecting the Gram type and the fermentative character of a bacterial strain, comprising:
  an illumination device configured to illuminate, in a wavelength range 390 nm-900 nm, at least one bacterium of the strain;
  a sensor configured to acquire, in the 390 nm-900 nm range, a luminous intensity reflected from or transmitted through the illuminated bacterium, wherein the illuminating by the sensor covers one or more wavelength ranges, wherein the one or more wavelength ranges cover at least two distinct spectral bands whose center wavelengths are more than 50 nm apart; and
  a computer unit configured to determine the Gram type and the fermentative character of the bacterial strain as a function of the luminous intensity acquired in the 390 nm-900 nm range, by applying an automated prediction model,
  wherein the prediction model includes at least one class identifying the Gram type of the bacteria strain,
  wherein the prediction model includes at least one class identifying the fermentative character of the bacterial strain,
  wherein the prediction model does not include a class identifying the microorganism at a species level.

26. The system as claimed in claim 25, configured to implement a process for detecting the Gram type and the fermentative character of a bacterial strain, comprising:
  illuminating in the wavelength range 390 nm-900 nm at least one bacterium of the strain having a natural electromagnetic response in the range, wherein the illuminating covers one or more wavelength ranges. wherein the one or more wavelength ranges cover at least two distinct spectral bands whose center wavelengths are more than 50 nm apart;
  acquiring, within the range, a luminous intensity reflected from or transmitted through the illuminated bacterium; and
  determining the Gram type and the fermentative character of the bacterial strain as a function of the acquired luminous intensity in the range,
  wherein the determination of Gram type and fermentative character comprises applying a classification of the prediction model predicting whether the acquired luminous intensity is the light intensity of a fermentative Gram-negative bacterial strain.

27. The system as claimed in claim 25, configured to illuminate, and acquire the image of, a sample comprising a colony of bacteria of the strain and a nutrient medium on which the colony has grown.

* * * * *